United States Patent [19]

Holland et al.

[11] 3,954,994
[45] May 4, 1976

[54] INTERMEDIATES FOR PREPARING HIPOLIPEMIC AGENTS AND METHOD OF LOWERING THE BLOOD LIPID LEVEL IN MAMMALS WITH SAID AGENTS

[75] Inventors: Gerald F. Holland, Old Lyme; Joseph G. Lombardino; Richard C. Koch, both of Niantic, all of Conn.

[73] Assignee: Pfizer Inc., New York, N.Y.

[22] Filed: July 31, 1973

[21] Appl. No.: 384,395

Related U.S. Application Data

[60] Division of Ser. No. 156,501, June 24, 1971, abandoned, and Ser. No. 156,502, June 24, 1971, abandoned, said Ser. No. 156,501, is a continuation of Ser. No. 764,951, Oct. 3, 1968, abandoned, which is a continuation-in-part of Ser. No. 723,321, April 22, 1968, abandoned, said Ser. No. 156,502, is a division of Ser. No. 764,951.

[52] U.S. Cl. ............................. 424/317; 424/244; 424/267; 424/274; 424/275; 424/308; 424/324
[51] Int. Cl.² ......................................... A61K 31/19
[58] Field of Search .............. 424/317; 156/501, 502

[56] References Cited

UNITED STATES PATENTS

| | | | |
|---|---|---|---|
| 3,502,717 | 3/1970 | Lombardino | 260/516 |
| 3,658,967 | 4/1972 | Leigh et al. | 424/317 |
| 3,706,792 | 12/1972 | Shen et al. | 260/52 D |

FOREIGN PATENTS OR APPLICATIONS

| | | | |
|---|---|---|---|
| 385,886 | 3/1965 | Switzerland | 260/516 |
| 1,911,539 | 10/1969 | Germany | 260/516 |
| 822,704 | 9/1969 | Canada | 424/317 |

OTHER PUBLICATIONS

Burger, Medicinal Chemistry, Wiley Interscience, N.Y., (1970), pp. 64, 71 and 72.
Yale, Journal of Medicinal and Pharmaceutical Chemistry, Vol. 1, No. 2 (1959), p. 121.

*Primary Examiner*—Frederick E. Waddell
*Attorney, Agent, or Firm*—Connolly and Hutz

[57] ABSTRACT

Intermediates for preparing benzylthio-, benzylsulfinyl-, and benzylsylfonyl-benzoic acids, and method of lowering the blood lipid level in mammals employing said acids.

10 Claims, No Drawings

INTERMEDIATES FOR PREPARING HIPOLIPEMIC AGENTS AND METHOD OF LOWERING THE BLOOD LIPID LEVEL IN MAMMALS WITH SAID AGENTS

CROSS-REFERENCE TO RELATED APPLICATIONS

This application is a division of application Ser. No. 156,501 filed June 24, 1971, now abandoned, which in turn is a continuation of application Ser. No. 764,951 filed Oct. 3, 1968 and now abandoned, which in turn is a continuation-in-part of application Ser. No. 723,321 filed Apr. 22, 1968 and now abandoned. This application is also a division of application Ser. No. 156,502 filed June 24, 1971, now abandoned, which in turn is a division of said application Ser. No. 764,951.

BACKGROUND OF THE INVENTION

This invention relates to intermediates for preparing benzylthio-, benzylsulfinyl-, and benzylsylfonyl-benzoic acids, and method of lowering the blood lipid level in mammals employing said acids.

Atherosclerosis, a form of arteriosclerosis, is characterized by internal thickening of the major blood vessels due to localized accumulation of lipids, of which cholesterol and other 8-lipoproteins, such as triglycerides, comprise the major constituents. Furthermore, it has been found that those suffering from the disease exhibit abnormally high blood cholesterol levels. While the etiology of the disease is not fully understood, it is believed that 8-lipoproteins, in particular cholesterol, play an important role.

In the advanced stages of the disease, plaques, comprising cholesterol and other β-lipoproteins, accumulate in the aorta, coronary, cerebral, and peripheral arteries of the lower extremities. As these plaques increase in size the danger of fibrin deposition, possibly resulting in thrombosis and occlusion, is enhanced.

While no sure method has been found for preventing the disease, it has been recommended that dietary habits be observed that will insure low β-lipoprotein levels. Besides stringent dietary management, various therapeutic agents such as estrogens, thyroxine analogs and sitosterol preparations have been used to lower the cholesterol levels of those afflicted with the condition.

It has now been found that various benzylthio-, benzylsulfiny-, and benzylsulfonylbenzoic acids are effective hypolipemic agents because of their ability to lower the blood lipid level of mammals. Consequently, these compounds can be expected to be useful in the treatment of atherosclerosis and related cardiovascular diseases which are associated with elevated blood lipid levels.

SUMMARY OF THE INVENTION

This invention comprises novel compounds having the formulae:

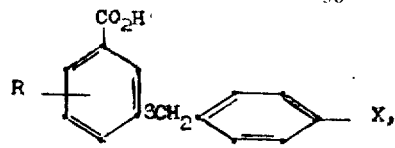
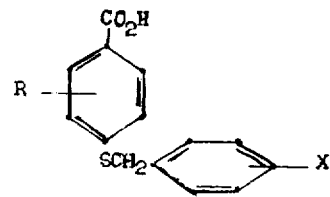
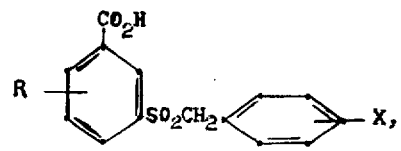
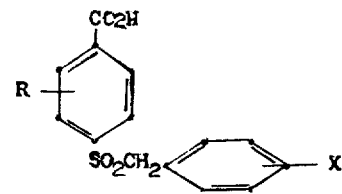
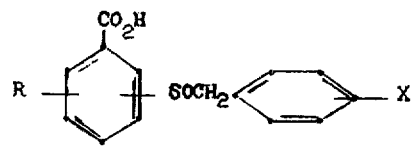
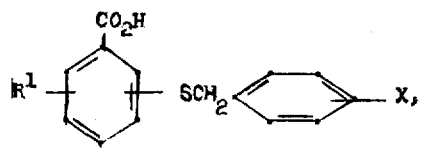
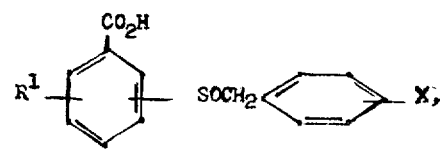
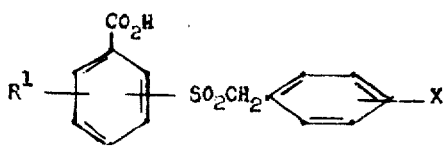

and

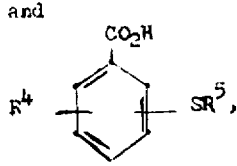 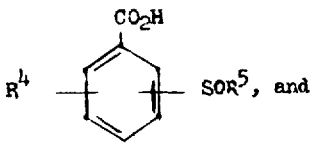 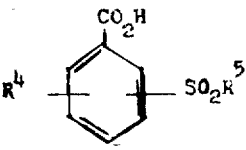

wherein
R is $CH_3$, $CF_3$, or $-NO_2$;
X is H, $-CH_3$, $CH_3O-$, $-NO_2$, Br, I, F, Cl, $-CF_3$ or $CF_3SO_2-$;
$R^1$ is Cl, Br, F, $-OCF_3$, $-OCH_3$, $CF_3SO_3-$, $(CH_3OCH_2CH_2)_2NSO_2-$, and $(R^2R^3)NSO_2-$,
wherein
$R^2$ and $R^3$ are H, alkyl up to 16 carbon atoms, aryl and arylalkyl up to 10 carbon atoms, and $R^2$ and $R^3$ taken together are polymethylene and alkylpolymethy-

provided that $R^6$ and $R^7$ are not both H when $n = 0$;
and the amides, lower alkyl esters, and salts thereof with bases.

This invention further comprises a method for lowering the blood lipid level in mammals by orally or parenterally administering a pharmaceutical composition containing a compound having the formula

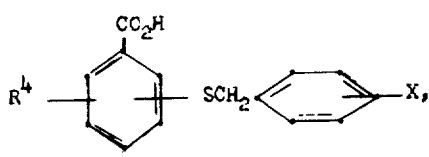 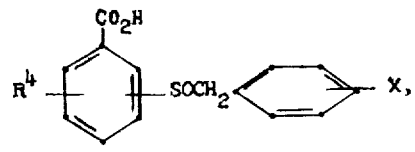

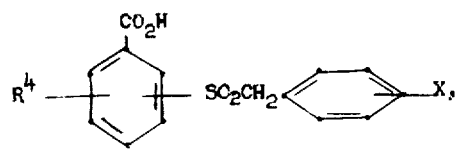 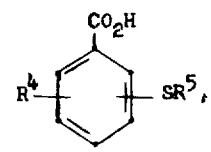

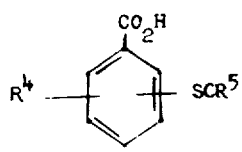 and 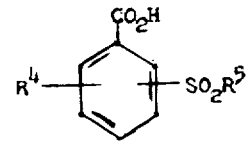

lene containing up to 15 carbon atoms, provided that $R^2$ and $R^3$ are not both N;

and $R^4$ is H, $-CH_3$, $-CF_3$, $-NO_2$, Cl, Br, F, $-OCH_3$, $-OCF_3$, $CF_3SO_2-$, $(CH_3OCH_2CH_2)_2NSO_2-$, and $(R^2R^3)NSO_2-$,
wherein
$R^2$ and $R^3$ are defined above. $R^5$ is where $R^4$, $R^5$ and X are as defined above;
and the amides, lower alkyl esters, and salts thereof with pharmaceutically acceptable bases.

DETAILED DESCRIPTION OF THE INVENTION

The compounds of the present invention are prepared by several independent procedures. In the procedure illustrated in Chart I, an appropriately substituted

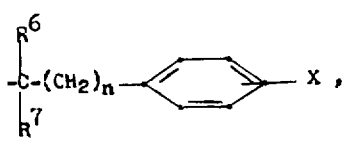 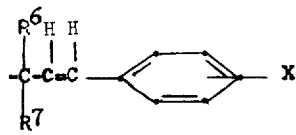

$-CH_2$-α-naphthyl, $-CH_2$-β-naphthyl, $-CH_2$α-thienyl, and $-CH_2$-β-thienyl wherein
X is as defined above;
$n = 0$-3;
$R^6$ and $R^7$ are H, lower alkyl up to 6 carbon atoms or benzyl mercaptan is reacted with either a halobenzonitrile or a halobenzoic acid in the presence of alkali, usually potassium or sodium hydroxide. In some cases, a small amount of copper catalyst is added to the reaction mixture.

Chart I

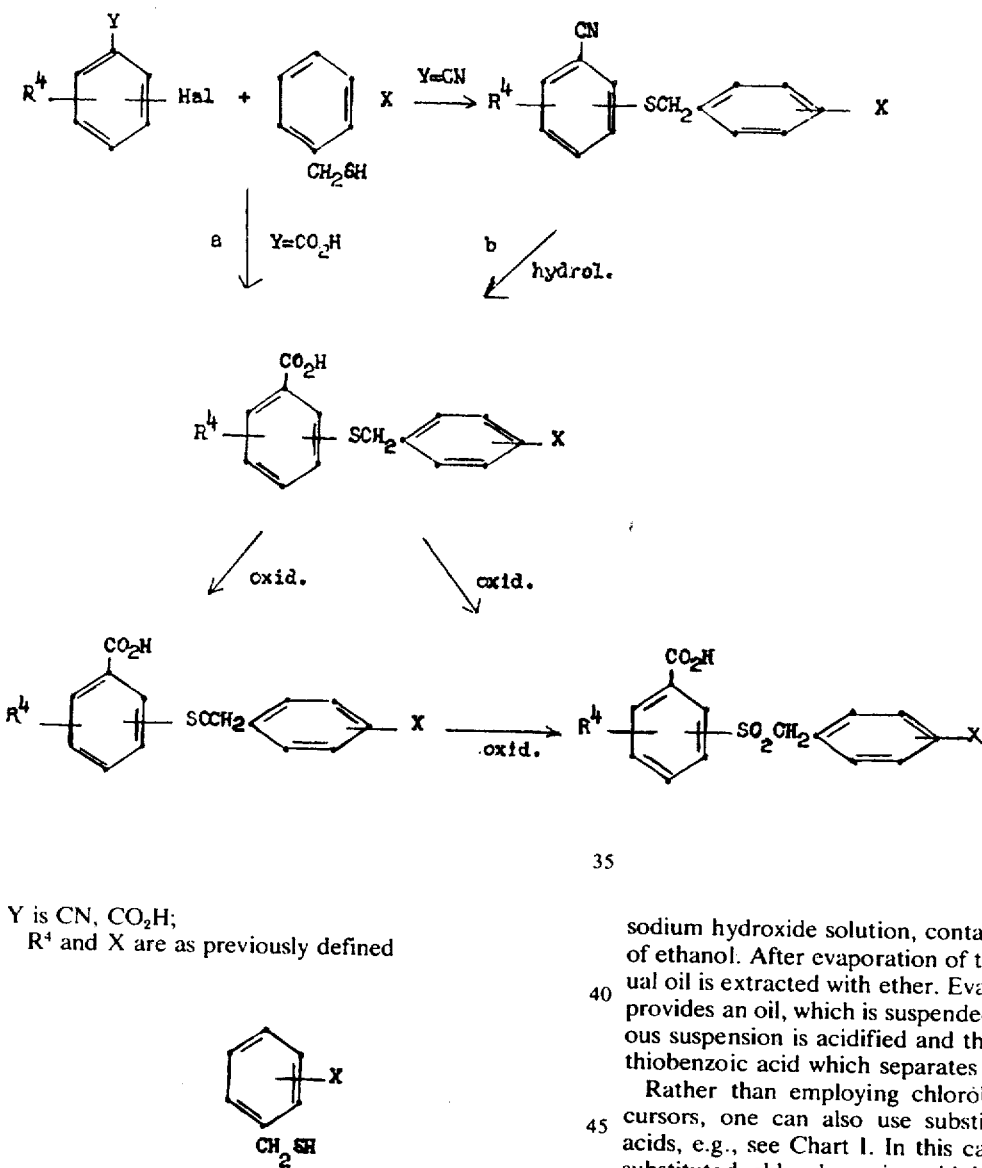

Y is CN, CO$_2$H;
R$^4$ and X are as previously defined can also be R$^5$ SH where R$^5$ is as previously defined.

When a chlorobenzonitrile is used as a precursor, the benzylmercaptide is usually prepared by treating the benzylmercaptan with an alkali metal alkoxide in a lower alkanol, e.g., sodium ethoxide in ethanol. The alkali metal benzylmercaptide is isolated and dissolved in anhydrous dimethylformamide. To this solution is then added the appropriately substituted chlorobenzonitrile (Chart I). After stirring the reaction mixture at room temperature to complete the reaction, it is poured into water, and the crude substituted benzylthiobenzonitrile is extracted with a suitable solvent, generally ether. The solvent is evaporated and the crude product is hydrolyzed by refluxing it in an aqueous sodium hydroxide solution, containing a small amount of ethanol. After evaporation of the ethanol, the residual oil is extracted with ether. Evaporation of the ether provides an oil, which is suspended in water. The aqueous suspension is acidified and the substituted benzylthiobenzoic acid which separates is collected.

Rather than employing chlorobenzonitriles as precursors, one can also use substituted chlorobenzoic acids, e.g., see Chart I. In this case the appropriately substituted chlorobenzoic acid is heated for several hours with a benzylmercaptan and a strong base, such as potassium hydroxide or sodium hydroxide, and usually a small amount of copper powder. The reaction mixture is cooled, filtered, and diluted with mineral acid and the substituted benzylthiobenzoic acid is isolated.

The benzylsulfinyl- and benzylsulfonylbenzoic acids are prepared by oxidation of the corresponding benzylthiobenzoic acids. If desired, one can prepare the benzylsulfonylbenzoic acids from the benzylsulfinylbenzoic acids by further oxidation. While these oxidations can be carried out with conventional oxidizing agents such as nitric acid, potassium permanganate, and chromium trioxide, we prefer to use hydrogen peroxide in either glacial acetic or formic acid.

An alternate synthetic route to the desired compounds of the instant invention is outlined in Chart 2.

Chart 2

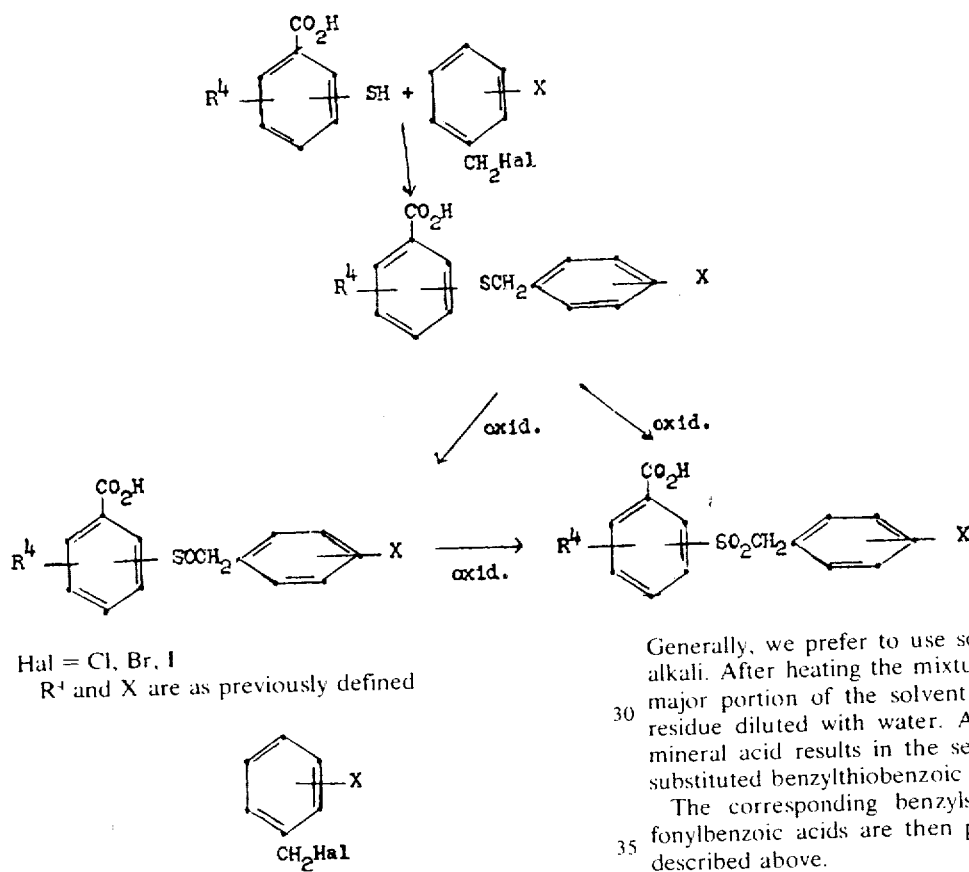

Hal = Cl, Br, I
R⁴ and X are as previously defined can also be R⁵Hal where R⁵ is as previously defined.

In the process outlined in Chart 2, one reacts a substituted mercaptobenzoic acid with a substituted benzyl halide in an alkaline, lower alkanol-water mixture. Generally, we prefer to use sodium carbonate as the alkali. After heating the mixture for a short time, the major portion of the solvent is evaporated and the residue diluted with water. Acidification with dilute mineral acid results in the separation of the desired substituted benzylthiobenzoic acid.

The corresponding benzylsulfinyl- and benzylsulfonylbenzoic acids are then prepared in the manner described above.

We have also developed a novel process for the preparation of the benzylsulfonylbenzoic acids of the present invention. This process is outlined in Chart 3.

Chart 3

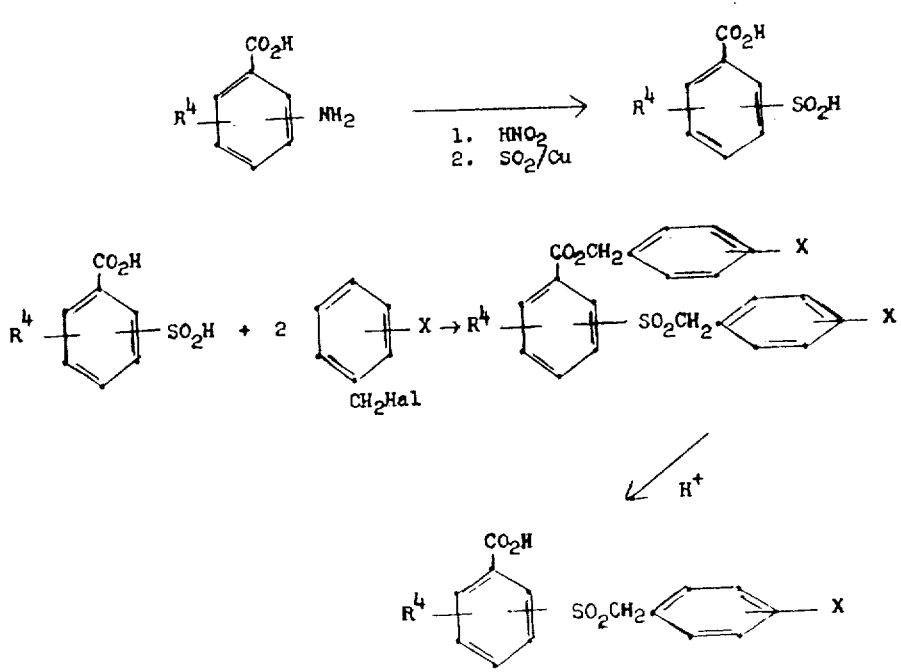

Hal = Cl, Br, I
R⁴ and X are as previously defined

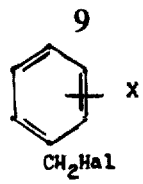

can also be R⁵Hal where R⁵ is as previously defined.

In this process the appropriate aminoaryl acid is diazotized in a tetrahydrofuran-water solution. Copper is suspended in the cold solution and sulfur dioxide is passed into the mixture with vigorous stirring. After standing for several hours the organic layer is separated and concentrated to a small volume. Chloroform is added and the mixture concentrated. The mixture is cooled and the sulfinobenzoic acid is filtered. This compound is then reacted in acetonitrile with a sufficient amount of the appropriate benzyl halide and a tertiary amine to yield the ester-sulfone (Chart 3). Hydrolysis of this latter product in acidic solution affords the desired benzylsulfonylbenzoic acid.

Most of the starting materials used to prepare the compounds of the present invention have been reported in literature. The benzyl- and cinnamyl halides employed herein as precursors are conveniently prepared from the appropriately substituted toluenes by methods well known to those skilled in the art. Thus, the benzyl and cinnamyl chloride can be readily synthesized by reaction of the corresponding appropriately substituted toluene or allylbenzene with chlorine, preferably with exposure to ultraviolet light. Alternatively, it may be prepared by reacting these compounds with sulfuryl chloride in the presence of a peroxide.

The benzyl and cinnamyl bromides can be similarly prepared from the corresponding toluenes and allylbenzenes by contacting them with elemental bromine in the presence of light. They can also be prepared by bromination in carbon tetrachloride with N-bromosuccinimide in the presence of a small amount of peroxide.

The requisite arylalkyl halides can also be prepared by halogenation, although a higher reaction temperature is required.

The necessary mercaptans are conveniently prepared from the corresponding halides by first heating the latter compounds with thiourea in absolute ethanol and then adding aqueous sodium hydroxide with further heating. The major portion of the ethanol is evaporated under reduced pressure and the residual aqueous solution is acidified, and the mercaptan extracted with ether and purified by conventional procedures.

The sulfamyl halobenzoic acids used in the procedure outlined in Chart I are prepared by chlorosulfonation of a halobenzoic acid, followed by treatment of the resultant product with the appropriate amine.

In the synthetic scheme outlined in Chart 1, the requisite reactive halo group can be introduced into the phenyl ring by diazotizing the amino group of an appropriately substituted aminobenzoic acid and treating the resultant diazonium salt with an inorganic halide. For example, the precursor, 3-iodo-5-trifluoromethylbenzoic acid is prepared by diazotizing 3-amino-5-trifluoromethylbenzoic acid and treating the resultant diazonium salt with potassium iodide.

The mercaptobenzoic acids used in the synthetic scheme outlined in Chart 2 are also prepared from the appropriate aryl diazonium salt. The diazonium salt can be reacted with either sodium sulfide to give an aryl disulfide, which when reduced with zinc dust and acetic acid gives the desired mercaptobenzoic acid, or alternatively, it can be reacted with potassium ethyl xanthate to give a phenyl dithiocarbonate, which when decomposed in alkaline solution, affords the desired product.

The amides, lower alkyl esters and various pharmaceutically acceptable salts of the compounds described in the present invention are also effective in lowering the lipid blood level of mammals. Although the pharmacological activity of the molecule resides in the anion, it is necessary to use a salt having a pharmaceutically acceptable cation. Such commonly employed cations include the ammonium, sodium, potassium, calcium, and magnesium ions. The pharmaceutically acceptable salts of the compounds described herein are prepared by conventional procedures, as for example, by adding the acid to an aqueous solution containing an equivalent amount of a pharmaceutically acceptable base, i.e., a base containing one of the above cations, followed by concentration of the resultant mixture to obtain the desired product. The bases may be selected from the hydroxides, oxides, carbonates, and bicarbonates. Although salts formed from pharmaceutically unacceptable bases are not useful therapeutically, they may be used in the purification of the compounds described herein and also for the preparation of the pharmaceutically acceptable salts.

For example, an impure acid can be purified by dissolving it in an aqueous solution containing a pharmaceutically unacceptable base and extracting the resultant solution of the pharmaceutically unacceptable salt with a suitable organic solvent to remove non-acidic organic impurities. The free, purified acid is then isolated by acidifying the solution and filtering the product. The acid can then be converted to a pharmaceutically acceptable salt as indicated above.

The esters and amides are also prepared by methods well known to those skilled in the art. Thus, the desired esters are conveniently prepared by refluxing the acids in the appropriate alcohol containing a small amount of acid as catalyst. Generally, any lower alkyl ester can be used, but for practical reasons no advantage is realized in preparing an ester from an alcohol having a molecular weight greater than butanol. The amides are conveniently prepared from the esters by treating the latter compounds in alcohol with ammonia.

As previously mentioned, the herein described benzylthio-, benzylsulfinyl-, and benzylsulfonylbenzoic acids, as well as their pharmaceutically acceptable salts, lower alkyl esters and amides, are effective hypolipemic agents, i.e., they lower the blood lipid level of mammals. This property has been dramatically demonstrated in rats. Groups, each comprising 4 animals, of normal Sprague-Dawley (Charles River) male rats weighing from 160–220 g. are fed rat chow containing 0.25 percent of the compounds described herein for two overnight feeding periods. On the morning of the third day the animals are anesthetized and bled from the abdominal aorta. The total plasma cholesterol is then determined by the method of J. J. Carr and I. J. Drekter reported in Clin. Chem., 2, 353 (1956). The plasma cholesterol level of the treated animals is found to be significantly reduced, when compared to animals not receiving the test compound.

The ability of the herein described compounds to lower the blood triglyceride level is illustrated by administering the compounds to dogs. A dosage level of 50–100 mg./kg. of the compound, in gelled capsules, is administered to dogs twice a day. This treatment is continued over a period of 2 weeks and on every second day, the cholesterol and triglyceride blood levels are determined. The chlolesterol level is determined by the method given above, and the triglyceride level is measured by the method of E. Van Handel and D. B. Zilversmith, reported in J. Lab. & Clin. Med., 50, 152 (1957).

Comparison of the blood triglyceride levels of dogs receiving the test compounds shows a significant reduction as compared to the triglyceride levels of untreated animals.

For oral administration in capsule form, the preferred excipients are lactose and high molecular weight polyethylene glycols. When aqueous suspensions are desired, the essential active ingredients are combined with emulsifying ingredients and/or suspending agents. Diluents such as ethanol, propylene glycol, glycerine and various combinations of diluents are employed.

A typical human dosage form for oral administration is as follows:

| | |
|---|---|
| 2-benzylthio-5-trifluoromethylbenzoic acid | 255.00 mg. |
| corn starch, dry | 17.50 mg. |
| lactose | 163.50 mg. |
| magnesium stearate | 17.10 mg. |
| sodium lauryl sulfate | 1.90 mg. |
| | 455.00 mg. |

The compounds described herein can be administered perenterally as well as orally. For purposes of parenteral administration, solutions and suspensions of the herein described compounds in sesame or peanut oil or in aqueous-propylene glycol can be employed. Of particular suitability are sterile aqueous solutions of the corresponding water-soluble salts previously described. These dosage forms are especially suitable for intramuscular and subcutaneous injection purposes. The aqueous solutions, including those of the salts dissolved in pure distilled water, are additionally useful for intravenous injection purposes provided that their pH be properly adjusted beforehand. Such solutions should also be suitably buffered, if necessary, and the liquid diluent first rendered isotonic with sufficient saline or glucose. In this connection, the sterile aqueous media employed are readily obtained by standard techniques well known to those in the art. For instance, distilled water is ordinarily used as the liquid diluent and the final preparation is passed through a suitable bacterial filter, such as a sintered-glass filter or a diatomaceous earth or unglazed porcelain filter. Preferred filters of this type include the Berkefeld, the Chamberland and the asbestos disc-metal Seitz filter, wherein the fluid is drawn throughout the filter candle into a sterile container with the aid of a suction pump. Needles to say, aseptic conditions must necessarily be maintained throughout such operations which are connected with the preparation of these injectable solutions.

The dosage required to lower the blood lipid level will be determined by the nature and the extent of the symptoms. Generally, small dosages will be administered initially with a gradual increase in dosage until the optimum level is determined. It will generally be found that when the composition is administered orally, larger quantities of the active ingredient will be required to produce the same level as produced by a smaller quantity administered parenterally. In general, from about 100 to 500 mg. of active ingredient per kilogram of body weight administered in single or multiple dosage units significantly lowers the blood lipid level. In general, when administered to humans orally or parenterally, the effective average daily dose is suitably between about 0.30 and 3.0 g. per day.

PREPARATION OF STARTING MATERIALS

A. General Procedure for the Preparation of Benzyl and Cinnamyl Mercaptans from the Corresponding Halides 0.50 Mole of the appropriate benzyl or cinnamyl halide is refluxed for about 3 hours with 0.50 mole of thiourea in about 250–400 ml. of absolute ethanol. About 300 ml. of a 10 percent sodium hydroxide solution is added to the resultant solution, and the resulting mixture is refluxed for another 2 hours.

The major portion of the ethanol is removed under reduced pressure. The aqueous mixture is cooled, acidified with sulfuric acid, and extracted with ether. The ether extracts are dried over anhydrous sodium sulfate, and evaporated. The residual crude mercaptan is then purified by conventional procedures.

B. Preparation of Sulfamylbenzoic Acids

To 31 g. (0.20 moles) of o-chlorobenzoic acid is added 117 g. (1.00 moles) of chlorosulfonic acid. The mixture is heated at 95°C. for 5 hours and kept at room temperature overnight. It is then cautiously poured into 400 ml. of ice water and the crude 2-chloro-5-chlorosulfonylbenzoic acid is filtered and washed with water (m.p. 147°–149°C.).

The crude acid is dissolved in 400 ml. of hot chloroform and dried first over sodium sulfate and then over magnesium sulfate. The solution is evaporated to dryness and the crude acid is added to 300 ml. of liquid ammonia contained in a 1 liter Erlenmeyer flask. The mixture is stirred until all the ammonia has evaporated. The gummy residue is then dissolved in water and the mixture acidified with 6N HCl. The m.p. of the filtered, crude 2-chloro-5-sulfamylbenzoic acid is 210°–212°C. After recrystallization from water the m.p. is 217°–219°C.; yield 19 g.

Employing the appropriate amines the following compounds are prepared according to the above procedure.

2-chloro-5-di-n-hexylsulfamylbenzoic acid
2-chloro-5-di-i-propylsulfamylbenzoic acid
2-chloro-5-diethylsulfamylbenzoic acid
2-chloro-5-dimethylsulfamylbenzoic acid
2-chloro-5-di-n-decylsulfamylbenzoic acid
2-chloro-5-di-n-dodecylsulfamylbenzoic acid
2-chloro-5-di-n-hexadecylsulfamylbenzoic acid
2-chloro-5-diphenylsulfamylbenzoic acid
2-chloro-5-di-p-tolylsulfamylbenzoic acid
2-chloro-5-dibenzylsulfamylbenzoic acid
2-chloro-5-di-($\beta$-p-tolylethyl)sulfamylbenzoic acid
2-chloro-5-di-($\alpha$-naphthyl)sulfamylbenzoic acid
2-chloro-5-N-phenyl-N-ethylsulfamylbenzoic acid
2-chloro-5-N-p-tolyl-N-n-hexadecylsulfamylbenzoic acid
2-chloro-5-N-benzyl-N-ethylsulfamylbenzoic acid
2-chloro-5-N-naphthyl-N-phenylsulfamylbenzoic acid
2-chloro-5-di-(p-isopropylbenzyl)sulfamylbenzoic acid
2-chloro-5-N-ethylsulfamylbenzoic acid
2-chloro-5-N-phenylsulfamylbenzoic acid
2-chloro-5-N-p-tolylsulfamylbenzoic acid The following acids are also obtained by means of this procedure:

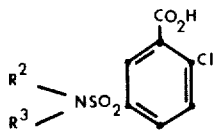

| $R^2$ and $R^3$ = | Compound |
|---|---|
| —CH₂CH₂— | 2-chloro-5-N,N-ethylene sulfamylbenzoic acid |
| —(CH₂)₄— | 2-chloro-5-N,N-tetramethylenesulfamylbenzoic acid |
| —(CH₂)₅— | 2-chloro-5-N,N-pentamethylenesulfamylbenzoic acid |
| —CH(C₂H₅)—(CH₂)₃—CH(C₂H₅)— | 2-chloro-5-N,N-(1′,5′-diethylpentamethylene sulfamylbenzoic acid |
| —(CH₂)₁₀— | 2-chloro-5-N,N-decamethylene sulfamylbenzoic acid |
| —(CH₂)₁₂— | 2-chloro-5-N,N-dodecamethylene sulfamylbenzoic acid |
| —CH(n-C₃H₇)—CH₂—CH(n-C₃H₇)—CH₂—CH(n-C₃H₇)— | 2-chloro-5-N,N-(1′,3′,5′-tri-n-propyl)pentamethylene sulfamylbenzoic acid |
| —CH(n-C₃H₇)—(CH₂)₇—CH(n-C₃H₇)— | 2-chloro-5-N,N-(1′,8′-di-n-propyl)-nonamethylene sulfamylbenzoic acid |
| —CH₂—CH(CH₃)—(CH₂)₂— | 2-chloro-5-N,N-(2′-methyl)tetramethylene sulfamylbenzoic acid |
| —CH₂—CH(C₂H₅)—(CH₂)₃— | 2-chloro-5-N,N-(2′-ethyl)pentamethylene sulfamylbenzoic acid |

C. Preparation of Activated Halobenzoic Acids 4.2 g. (0.0205 moles) of 3-amino-5-trifluoromethylbenzoic acid is added to mixture of 35 ml. of water and a mixture ml. of 6N sulfuric acid. The mixture is heated on the steam bath for several minutes and cooled to 3°C. A solution of 1.5 g. (0.0217 moles) of sodium nitrite in 10 ml. of water is added to this mixture over the course of 10 minutes. The resultant mixture is stirred for 1 hour at a temperature below 5°C.

The above mixture is then added to a solution of 9.3 g. of potassium iodide in 10 ml. of water containing 50 mg. of copper metal. The resultant mixture is stirred at room temperature for 1 hour and then heated to boiling and stirred at this temperature for 15 minutes. The mixture is filtered and the crude 3-iodo-5-trifluoromethylbenzoic acid is washed with water. Yield 5.2 g. The crude acid is purified by sublimation at 135°C./0.05 mm. M.p. 180°–181°C.; yield 4.5 g.

| Anal. | Calc'd for C₈H₄F₃IO₂: | C, 30.40; H, 1.28. |
|---|---|---|
| | Found: | C, 30.74; H, 1.14. |

The following compounds are also prepared by the above procedure.

3-nitro-5-iodobenzoic acid
3-trifluoromethoxy-5-iodobenzoic acid
3-trifluoromethylsulfonyl-5-iodobenzoic acid
3-dimethylsulfamyl-5-iodobenzoic acid
3-di-n-butylsulfamyl-5-iodobenzoic acid
3-di-n-hexylsulfamyl-5-iodobenzoic acid
3-di-n-hexylsulfamyl-5-iodobenzoic acid
3-di-i-propylsulfamyl-5-iodobenzoic acid
3-diethylsulfamyl-5-iodobenzoic acid
3-dimethylsulfamyl-5-iodobenzoic acid
3-di-n-decylsulfamyl-5-iodobenzoic acid
3-di-n-dodecylsulfamyl-5-iodobenzoic acid
3-di-n-hexadecylsulfamyl-5-iodobenzoic acid
3-diphenylsulfamyl-5-iodobenzoic acid
3-di-p-tolylsulfamyl-5-iodobenzoic acid
3-dibenzylsulfamyl-5-iodobenzoic acid
3-di-(β-p-tolylethyl)sulfamyl-5-iodobenzoic acid
3-di-(α-naphthyl)sulfamyl-5-iodobenzoic acid
3-N-phenyl-N-ethylsulfamyl-5-iodobenzoic acid
3-N-p-tolyl-N-n-hexadecylsulfamyl-5-iodobenzoic acid
3-N-benzyl-N-ethylsulfamyl-5-iodobenzoic acid
3-N-naphthyl-N-phenylsulfamyl-5-iodobenzoic acid
3-di-(p-isopropylbenzyl)sulfamyl-5-iodobenzoic acid
3-N,N-ethylenesulfamyl-5-iodobenzoic acid
3-N,N-tetramethylenesulfamyl-5-iodobenzoic acid
3-N,N-pentamethylenesulfamyl-5-iodobenzoic acid
3-N,N-(1′,5′-diethylpentamethylenesulfamyl-5-iodobenzoic acid
3-N,N-decamethylenesulfamyl-5-iodobenzoic acid
3-N,N-dodecamethylenesulfamyl-5-iodobenzoic acid
3-N,N-(1′,3′,5′-tri-n-propyl)pentamethylenesulfamyl-5-iodobenzoic acid
3-N,N-(1′,8′-di-n-propyl)nonamethylenesulfamyl-5-iodobenzoic acid
3-N,N-(2′-methyl)tetramethylenesulfamyl-5-iodobenzoic acid
3N,N-(2′-ethyl)pentamethylenesulfamyl-5-iodobenzoic acid
3-N-ethysulfamyl-5-iodobenzoic acid
3-N-phenylsulfamyl-5-iodobenzoic acid
3-N-p-tolylsulfamyl-5-iodobenzoic acid

D. Preparation of Mercaptobenzoic Acids

1. Mercaptobenzoic Acids from the Aryl Disulfides

To 95 ml. of boiling water is added 86 g. (0.355 moles) of Na₂S.9H₂O and 11.2 g. of powdered sulfur. After solution is complete, 13 g. of sodium hydroxide (0.33 moles) in 33 ml. of water is added and the resultant solution is cooled to 0°C. and set aside.

To a mixture of 165 ml. of water and 66 ml. of concentrated hydrochloric acid is added 50 g. (0.331 moles) of 5-methylanthranilic acid. The mixture is cooled to about 0°C. and a solution of 23 g. (0.331 moles) of sodium nitrite in 93 ml. of water is added with vigorous stirring beneath the surface of the mixture over a period of about 10 minutes. Care is taken to keep the temperature of the mixture below 5°C. and to this end about 200 g. of cracked ice is added during the addition of the sodium nitrite solution.

This latter solution is then added to the first solution prepared above at 0°C. over a period of from 20 to 30 minutes. During the addition, sufficient ice is added to maintain the temperature of the mixture at about 0°C.

The resultant solution is then allowed to warm to room temperature and stirred for 2 hours. It is then acidified to the Congo Red endpoint with about 50 ml. of concentrated hydrochloric acid. The crude 2,2'-dicarboxy-di-4-tolydisulfide which separates is collected and washed with water. The sulfur impurities it contains are removed by dissolving it in a solution of 20 g. of sodium carbonate in 660 ml. of water, heating the mixture, and filtering the sulfur residue. The filtrate is acidified with concentrated hydrochloric acid and the precipitated product separated and dried to afford 66 g. of 2,2'-dicarboxy-di-4-tolyl disulfide.

The entire amount of this latter compound is added to a mixture of 45 g. of zinc dust in 500 ml. of glacial acetic acid. The resultant mixture is refluxed for about 4 hours, cooled, and the crude acid filtered. The crude product is dissolved in hot, aqueous sodium hydroxide solution and the resultant solution is filtered. The filtrate is cooled, acidified with concentrated hydrochloric acid, and the acid (5-methyl-2-mercaptobenzoic acid) that separates is collected, washed with water, and dried in a vacuum oven at 45°C. The yield is 23 g., m.p. 163°–164°C.

The following acids are also prepared by this method from the appropriate starting materials:

5-chloro-2-mercaptobenzoic acid
5-bromo-2-mercaptobenzoic acid
5-fluoro-2-mercaptobenzoic acid
5-trifluoromethyl-2-mercaptobenzoic acid
5-methoxy-2-mercaptobenzoic acid
5-trifluoromethylsulfonyl-2-mercaptobenzoic acid
5-nitro-2-mercaptobenzoic acid
5-trifluoromethoxy-2-mercaptobenzoic acid
5-di-n-hexylsulfamyl-2-mercaptobenzoic acid
5-di-n-hexadecylsulfamyl-2-mercaptobenzoic acid
5-diphenylsulfamyl-2-mercaptobenzoic acid
5-dibenzylsulfamyl-2-mercaptobenzoic acid
5-N-phenyl-N-ethylsulfamyl-2-mercaptobenzoic acid
5-N-benzyl-N-ethylsulfamyl-2-mercaptobenzoic acid
5-N,N-tetramethylenesulfamyl-2-mercaptobenzoic acid
5-N,N-pentamethylenesulfamyl-2-mercaptobenzoic acid
5-N,N-(2'-methyl)tetramethylenesulfamyl-2-mercaptobenzoic acid
5-N,N-(2'-ethyl)pentamethylenesulfamyl-2-mercaptobenzoic acid
4-chloro-2-mercaptobenzoic acid
4-bromo-2-mercaptobenzoic acid
4-fluoro-2-mercaptobenzoic acid
4-trifluoromethyl-2-mercaptobenzoic acid
4-methoxy-2-mercaptobenzoic acid
4-trifluoromethylsulfonyl-2-mercaptobenzoic acid
4-nitro-2-mercaptobenzoic acid
4-trifluoromethoxy-2-mercaptobenzoic acid
4-di-n-hexylsulfamyl-2-mercaptobenzoic acid
4-di-n-hexadecylsulfamyl-2-mercaptobenzoic acid
4-diphenylsulfamyl-2-mercaptobenzoic acid
4-dibenzylsulfamyl-2-mercaptobenzoic acid
4-N-phenyl-N-ethylsulfamyl-2-mercaptobenzoic acid
4-N-benzyl-N-ethylsulfamyl-2-mercaptobenzoic acid
4-N,N-tetramethylenesulfamyl-2-mercaptobenzoic acid
4-N,N-pentamethylenesulfamyl-2-mercaptobenzoic acid
4-N,N-(2'-methyl)tetramethylenesulfamyl-2-mercaptobenzoic acid
4-N,N-(2'-ethyl)pentamethylenesulfamyl-2-mercaptobenzoic acid
5-chloro-3-mercaptobenzoic acid
5-bromo-3-mercaptobenzoic acid
5-fluoro-3-mercaptobenzoic acid
5-trifluoromethyl-3-mercaptobenzoic acid
5-methoxy-3-mercaptobenzoic acid
5-N-ethylsulfamyl-3-mercaptobenzoic acid
5-N-phenylsulfamyl-3-mercaptobenzoic acid
5-N-p-tolylsulfamyl-3-mercaptobenzoic acid
5-trifluoromethylsulfonyl-3-mercaptobenzoic acid
5-nitro-3-mercaptobenzoic acid
5-trifluoromethoxy-3-mercaptobenzoic acid
5-di-n-hexylsulfamyl-3-mercaptobenzoic acid
5-di-n-hexadecylsulfamyl-3-mercaptobenzoic acid
5-diphenylsulfamyl-3-mercaptobenzoic acid
5-dibenzylsulfamyl-3-mercaptobenzoic acid
5-N-phenyl-N-ethylsulfamyl-3-mercaptobenzoic acid
5-N-benzyl-N-ethylsulfamyl-3-mercaptobenzoic acid
5-N,N-tetramethylenesulfamyl-3-mercaptobenzoic acid
5-N,N-pentamethylenesulfamyl-3-mercaptobenzoic acid
5-N,N-(2'-methyl)tetramethylenesulfamyl-3-mercaptobenzoic acid
5-N,N-(2'-ethyl)pentamethylenesulfamyl-3-mercaptobenzoic acid
3-chloro-4-mercaptobenzoic acid
3-bromo-4-mercaptobenzoic acid
3-fluoro-4-mercaptobenzoic acid
3-trifluoromethyl-4-mercaptobenzoic acid
3-methoxy-4-mercaptobenzoic acid
3-trifluoromethylsulfonyl-4-mercaptobenzoic acid
3-nitro-4-mercaptobenzoic acid
3-trifluoromethoxy-4-mercaptobenzoic acid
3-di-n-hexylsulfamyl-4-mercaptobenzoic acid
3-di-n-hexadecylsulfamyl-4-mercaptobenzoic acid
3-diphenylsulfamyl-4-mercaptobenzoic acid
3-dibenzylsulfamyl-4-mercaptobenzoic acid
3-N-phenyl-N-ethylsulfamyl-4-mercaptobenzoic acid
3-N-benzyl-N-ethylsulfamyl-4-mercaptobenzoic acid
3-N,N-tetramethylenesulfamyl-4-mercaptobenzoic acid
3-N,N-pentamethylenesulfamyl-4-mercaptobenzoic acid
3-N,N-(2'-methyl)tetramethylenesulfamyl-4-mercaptobenzoic acid
3-N,N-(2'-ethyl)pentamethylenesulfamyl-4-mercaptobenzoic acid 2. Mercaptobenzoic Acids from the aryl ethyl dithiocarbonates To a mixture comprising 48 ml. of 1 N hydrochloric acid and 70 ml. of methanol is added 4.1 g. of 2-amino-4-trifluoromethylbenzoic acid (0.02 moles). The resultant mixture is cooled to about 3°C. and 1.4 g. (0.02 moles) of sodium nitrite dissolved in 15 ml. of water is added over the course of about 5 minutes. During the addition the temperature of the mixture is kept below 5°C. The resultant mixture is stirred at about 4°–5°C. for an additional 10 minutes and then added over a period of 5 minutes to a solution of 3.7 g. (0.023 moles) of potassium ethyl xanthate and 1.3 g. of potassium hydroxide (0.02 moles) in 50 ml. of water, which has been previously heated to about 40°C. During the addition the temperature of the reaction mixture is kept between 35°C. and 40°C. After the addition is complete, the resultant mixture is stirred at 40°C. for ½ hour. The methanol is evaporated at 40°C. and the residual solution is acidified with concentrated hydrochloric acid and extracted with ether. The ether extract is separated, washed with water and evaporated to dryness. The residue is triturated with 20 ml. of n-hexane and filtered to give 1.4 g. of 2-carboxy-5-trifluoromethylphenyl ethyl dithiocarbonate.

To a solution of 5 g. of sodium hydroxide in 20 ml. of water is added 3.4 g. of 2-carboxy-5-trifuloromethylphenyl ethyl dithiocarbonate. The mixture is refluxed under a nitrogen atmosphere for 4 ½ hours and filtered. The filtrate is acidified with concentrated hydrochloric acid and the 2-mercapto-4-trifluoromethylbenzoic acid which precipitates from solution is isolated and washed first with water and then n-hexane. After drying in the oven, 2.4 g. of product are obtained; m.p. 157°–162°C.

The mercaptobenzoic acids in D 1 above are also prepared according to this procedure.

The following examples are provided to more fully illustrate the present invention, but are not to be construed as limiting the scope thereof.

EXAMPLE I

Into 100 ml. of ethanol is added 12.4 g. (0.10 moles) of benzylmercaptan. While nitrogen is bubbled into the solution, 100 ml. of a 1 molar sodium ethoxide in ethanol solution is added. The solvent is evaporated and 100 ml. of anhydrous dimethylformamide is added to the crude solid sodium mercaptide. To the resulting solution is then added 21 g. (0.10 moles) of 4-chloro-3-cyanobenzotrifluoride. The reaction mixture is stirred under nitrogen at room temperature for ½ hour and then poured into about 800 ml. of ice-water. After stirring this mixture for 5 minutes, it is extracted with four 200 ml.-portions of ether.

The extracts are combined, dried over anhydrous sodium sulfate and evaporated to provide, after drying under high vacuum, a pale yellow oil that crystallizes to a solid upon standing. The yield of crude 2-benzylthio-5-trifluoromethylbenzonitrile is 27.4 g. (94 percent).

In about 15 ml. of ethanol is dissolved 17.5 g. (0.06 moles) of the crude 2-benzylthio-5-trifluoromethylbenzonitrile. To this solution is added 200 ml. of 20 percent sodium hydroxide solution.

The reaction mixture is refluxed for about 27 hours. After removing the major portion of the ethanol under reduced pressure, the residual oil present in the aqueous phase is extracted with three 200 ml.-portions of ether. After the ether extracts are combined and evaporated, the residual oil is suspended in about 500 ml. of water. This suspension is acidified with 6 N hydrochloric acid and the white solid that separates is filtered. The yield of 2-benzylthio-5-trifluoromethylbenzoic acid is 15.7 g. (84%); m.p. 169°–174°C. Upon recrystallization from benzene, the melting point is 180°–181°C.

| | Neutralization Equivalent: | 315 |
|---|---|---|
| | Theoretical: | 312 |
| Anal. | Calc'd for $C_{15}H_{11}F_3O_2S$: | C, 57.68; H, 3.55. |
| | Found: | C, 57.46; H, 3.64 |

Using the appropriate precursors, the following compounds are prepared according to the above procedure.

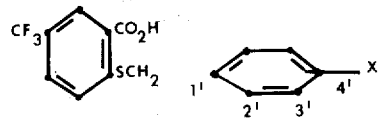

| X | M.p., °C. | Elemental Analysis | | | |
|---|---|---|---|---|---|
| | | Calculated | | Found | |
| | | C | H | C | H |
| 3'-methyl | 192–195 | — | — | — | — |
| 4'-chloro | 183–184.5 | 51.95 | 2.91 | 52.24 | 2.91 |
| 4'-methyl | 177–178.5 | 58.89 | 4.01 | 59.12 | 4.22 |
| 4'-methoxy | 174–175.5 | 56.13 | 3.83 | 56.53 | 3.90 |
| 2'-methoxy | 207–209 | 56.13 | 3.83 | 56.10 | 3.80 |
| 3'-chloro | 160–161.5 | 51.95 | 2.91 | 51.75 | 3.01 |
| 3'-trifluoromethyl | 165–166 | 50.53 | 3.27 | 50.34 | 3.18 |

2-(α-naphthylmethylenethio)-5-trifluoromethylbenzoic acid; m.p. 229–231
Anal.  Calc'd for $C_{19}H_{13}F_3O_2S$:   C, 63.33; H, 3.63.
           Found:                                        C, 63.20; H, 3.67.

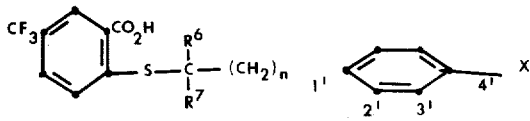

| | | | | | Elemental Analysis | | | |
|---|---|---|---|---|---|---|---|---|
| | | | | | Calculated | | Found | |
| n | $R^6$ | $R^7$ | X | M.p.,°C. | C | H | C | H |
| 0 | H | $CH_3$ | H | 140–142 | 58.89 | 4.01 | 58.61 | 4.07 |
| 1 | H | H | H | 161–162 | 58.89 | 4.01 | 59.25 | 4.06 |
| 0 | H | $C_2H_5$ | | 134–139 | 59.99 | 4.44 | 60.05 | 4.50 |

-continued

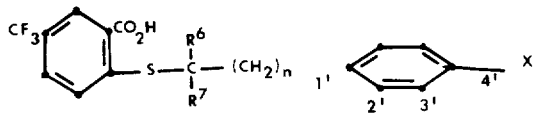

| X | | | M.p., °C. | Elemental Analysis | | | |
|---|---|---|---|---|---|---|---|
| | | | | Calculated | | Found | |
| | | | | C | H | C | H |
| 2 | H | H | H | 138–140 | 59.99 | 4.44 | 60.02 | 4.85 |

The following compounds are also prepared from the appropriate precursors according to the above procedure:

2-3'-trifluoromethylbenzylthiobenzoic acid
2-benzylthiobenzoic acid
3-benzylthiobenzoic acid
3-4'-chlorobenzylthiobenzoic acid
2-4'-bromobenzylthio-5-trifluoromethylbenzoic acid
2-2'-fluorobenzylthio-5-trifluoromethylbenzoic acid
2-4'-nitrobenzylthio-5-trifluoromethylbenzoic acid
2-4'-trifluoromethylsulfonylbenzylthio-5-trifluoromethylbenzoic acid
2-3'-iodobenzylthio-5-trifluoromethylbenzoic acid
2-(β-naphthylmethylenethio)-5-trifluoromethylbenzoic acid
2-(α-thienylmethylenethio)-5-trifluoromethylbenzoic acid
2-(β-thienylmethylenethio)-5-trifluoromethylbenzoic acid

| $R^6$ | $R^7$ | n | X |
|---|---|---|---|
| n-$C_6H_{13}$ | H | 0 | 3-Cl |
| $CH_3$ | $CH_3$ | 0 | 4-$CF_3$ |
| $C_6H_5$ | $C_6H_5$ | 0 | 4-Br |
| 4'-Cl$C_6H_4$ | 4'-Cl$C_6H_4$ | 0 | 4-$CH_3O$ |
| 4'-tolyl | 4'-tolyl | 0 | 2-$CH_3O$ |
| 4'-$CH_3OC_6H_4$ | 4'-$CH_3OC_6H_4$ | 0 | 4-$CH_3$ |
| 3'-$CF_3C_6H_4$ | 3'-$CF_3C_6H_4$ | 0 | 3-I |
| 4'-$NO_2C_6H_4$ | 4'-$NO_2C_6H_4$ | 0 | 4-F |
| $C_2H_5$ | H | 1 | 3-$CF_3SO_2$ |
| n-$C_4H_9$ | $CH_3$ | 1 | 4-$NO_2$ |
| $C_6H_5$ | $CH_3$ | 1 | 3-$CF_3SO_2$ |
| 4'-tolyl | $C_6H_5$ | 1 | 3-F |
| $C_2H_5$ | $C_6H_5$ | 2 | H |
| 3'-$CH_3OC_6H_4$ | $C_6H_5$ | 2 | 4-$CH_3$ |
| 4'-Br$C_6H_4$ | 4'-Br$C_6H_4$ | 2 | H |
| 2'-$CH_3OC_6H_4$ | 4'-F$C_6H_4$ | 2 | 2-F |
| H | H | 3 | H |
| n-$C_5H_{11}$ | $CH_3$ | 3 | 4-$CF_3SO_2$ |
| $C_6H_5$ | $C_6H_5$ | 3 | 2-$CH_3$ |
| H | $C_6H_5$ | 3 | 3-$CF_3$ |
| 4'-Cl$C_6H_4$ | 4'-tolyl | 3 | 3-$NO_2$ |

EXAMPLE II

To 250 ml. of dimethylformamide, under nitrogen, are added 10.1 g. (0.05 moles) of 2-chloro-5-nitrobenzoic acid, 7.3 g. (0.05 moles) of m-methylbenzyl mercaptan, 150 mg. of copper powder and 6.6 g. of potassium hydroxide.

The resulting brown-yellow suspension is heated in an oil bath at 125°C. for about 16 hours. The reaction mixture is cooled and filtered. The filtrate is poured into about 500 ml. of cold 6 N HCl and the yellow precipitate that forms is filtered and washed with water. The yield is 10.3 g. (66%). This material is recrystallized from ethanol to provide 3.7 g. (36%) of 2-3'-methylbenzylthio-5-nitrobenzoic acid; m.p. 238°–240°C.

| Anal. | Calc'd for $C_{15}H_{13}NO_4S$: | C, 59.2; H, 4.27; N, 4.58. |
|---|---|---|
| | Found: | C, 59.68; H, 4.49; N, 4.56. |

Employing the appropriately substituted benzyl mercaptans and starting materials the following compounds are readily prepared.

2-benzylthio-5-nitrobenzoic acid
2-3'-methoxybenzylthio-5-nitrobenzoic acid
2-4'-bromobenzylthio-5-nitrobenzoic acid
2-4'-chlorobenzylthio-5-nitrobenzoic acid
2-3'-fluorobenzylthio-5-nitrobenzoic acid
2-3'-iodobenzylthio-5-nitrobenzoic acid
2-4'-nitrobenzylthio-5-nitrobenzoic acid
2-4'-trifluoromethylsulfonylbenzylthio-5-nitrobenzoic acid
2-3'-trifluoromethylbenzylthio-5-nitrobenzoic acid
2-(α-naphthylmethylenethio)-5-nitrobenzoic acid
2-(β-naphthylmethylenethio)-5-nitrobenzoic acid
2-(α-thienylmethylenethio)-5-nitrobenzoic acid
2-(β-thienylmethylenethio)-5-nitrobenzoic acid
2-benzylthio-5-trifluoromethoxybenzoic acid
2-3'-methylbenzylthio-5-trifluoromethoxybenzoic acid
2-4'-trifluoromethylbenzylthio-5-trifluoromethoxybenzoic acid
2-3'-nitrobenzylthio-5-trifluoromethoxybenzoic acid
2-2'-fluorobenzylthio-5-trifluoromethoxybenzoic acid
2-3'-methoxybenzylthio-5-trifluoromethoxybenzoic acid
2-4'-chlorobenzylthio-5-trifluoromethoxybenzoic acid
2-4'-bromobenzylthio-5-trifluoromethoxybenzoic acid
2-4'-iodobenzylthio-5-trifluoromethoxybenzoic acid
2-3'-trifluoromethylsulfonylbenzylthio-5-trifluoromethoxybenzoic acid
2-(α-naphthylmethylenethio)-5-nitrobenzoic acid
2-(β-naphthylmethylenethio)-5-nitrobenzoic acid
2-(α-thienylmethylenethio)-5-nitrobenzoic acid
2-(β-thienylmethylenethio)-5-nitrobenzoic acid 2-benzylthio-5-trifluoromethylsulfonylbenzoic acid
2-3'-methylbenzylthio-5-trifluoromethylsulfonylbenzoic acid
2-4'-trifluoromethylbenzylthio-5-trifluoromethylsulfonylbenzoic acid
2-3'-nitrobenzylthio-5-trifluoromethylsulfonylbenzoic acid
2-2'-fluorobenzylthio-5-trifluoromethylsulfonylbenzoic acid
2-3'-methoxybenzylthio-5-trifluoromethylsulfonylbenzoic acid
2-4'-chlorobenzylthio-5-trifluoromethylsulfonylbenzoic acid
2-4'-bromobenzylthio-5-trifluoromethylsulfonylbenzoic acid
2-4'-iodobenzylthio-5-trifluoromethylsulfonylbenzoic acid
2-3'-trifluoromethylsulfonylbenzylthio-5-trifluoromethylsulfonylbenzoic acid
2-(α-naphthylmethylenethio)-5-nitrobenzoic acid
2-(β-naphthylmethylenethio)-5-nitrobenzoic acid
2-(α-thienylmethylenethio)-5-nitrobenzoic acid
2-(β-thienylmethylenethio)-5-nitrobenzoic acid oxide. To the mixture is then added 1.05 g. (0.02 moles) sodium methoxide and 3.0 g. (0.02 moles) of cinnamylmercaptan in 10 ml. of dimethylformamide.

The reaction mixture is heated at 85°C. for 1 ½ hours, cooled to room temperature and added to 100 ml. of water. The resultant mixture is then added dropwise to a solution of 5 ml. of concentrated hydrochloric acid in 200 ml. of water.

The 2-(cinnamylthio)-5-trifluoromethylbenzoic acid that separates is filtered and dissolved in ether. The ether solution is dried over anhydrous sodium sulfate, treated with charcoal and concentrated. n-Hexane is added to the solution and the 2-(cinnamylthio)-5-trifluoromethylbenzoic acid which separates from solution is filtered. Yield 1.3 g; m.p. 190°–191.5°C. An additional crop of crystals is obtained, (900 mg.; m.p. 190–191.5).

Recrystallization from ether - n-hexane gives m.p. of 190°–191.5°C.

| Anal. | Calc'd for $C_{17}H_{13}F_3O_3S$: | C, 60.34; H, 3.87. |
|---|---|---|
| | Found: | C, 60.39; H, 4.02 |

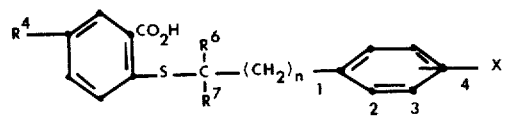

| $R^4$ | $R^6$ | $R^7$ | n | X |
|---|---|---|---|---|
| $NO_2$ | $CH_3$ | $CH_3$ | 0 | 3-Cl |
| $NO_2$ | $C_6H_5$ | $C_6H_5$ | 0 | 4-$CH_3O$ |
| $NO_2$ | n-$C_6H_{13}$ | H | 0 | 3-$CF_3SO_2$ |
| $NO_2$ | 4'-tolyl | 4'-tolyl | 1 | 2-$CH_3O$ |
| $NO_2$ | 3'-$CF_3C_6H_4$ | 3'-$CF_3C_6H_4$ | 1 | 3-I |
| $NO_2$ | n-$C_4H_9$ | 4'-$ClC_6H_4$ | 1 | 3-F |
| $NO_2$ | $C_2H_5$ | $C_2H_5$ | 2 | H |
| $NO_2$ | 4'-$BrC_6H_4$ | 4'-$FC_6H_4$ | 2 | 4-$CH_3$ |
| $NO_2$ | 2'-$CH_3OC_6H_4$ | 4'-tolyl | 2 | 3-Br |
| $NO_2$ | H | H | 3 | H |
| $NO_2$ | H | $C_6H_5$ | 3 | 2-$CF_3$ |
| $NO_2$ | 4'-$ClC_6H_4$ | 4'-$CF_3C_6H_4$ | 3 | 3-$NO_2$ |
| $CF_3O$ | $CH_3$ | $CH_3$ | 0 | 3-Cl |
| $CF_3O$ | $C_6H_5$ | $C_6H_5$ | 0 | 4-$CH_3O$ |
| $CF_3O$ | n-$C_6H_{13}$ | H | 0 | 3-$CF_3SO_2$ |
| $CF_3O$ | 4'-tolyl | 4'-tolyl | 1 | 2-$CH_3O$ |
| $CF_3O$ | 3'-$CF_3C_6H_4$ | 3'-$CF_3C_6H_4$ | 1 | 3-I |
| $CF_3O$ | n-$C_4H_9$ | 4'-$ClC_6H_4$ | 1 | 3-F |
| $CF_3O$ | $C_2H_5$ | $C_2H_5$ | 2 | H |
| $CF_3O$ | 4'-$BrC_6H_4$ | 4'-$FC_6H_4$ | 2 | 4-$CH_3$ |
| $CF_3O$ | 2'-$CH_3OC_6H_4$ | 4'-tolyl | 2 | 3-Br |
| $CF_3O$ | H | H | 3 | H |
| $CF_3O$ | H | $C_6H_5$ | 3 | 2-$CF_3$ |
| $CF_3O$ | 4'-$ClC_6H_4$ | 4'-$CF_3C_6H_4$ | 3 | 3-$NO_2$ |
| $CF_3SO_2$ | $CH_3$ | $CH_3$ | 0 | 3-Cl |
| $CF_3SO_2$ | $C_6H_5$ | $C_6H_5$ | 0 | 4-$CH_3O$ |
| $CF_3SO_2$ | n-$C_6H_{13}$ | H | 0 | 3-$CF_3SO_2$ |
| $CF_3SO_2$ | 4'-tolyl | 4'-tolyl | 1 | 2-$CH_3O$ |
| $CF_3SO_2$ | 3'-$CF_3C_6H_4$ | 3'-$CF_3C_6H_4$ | 1 | 3-I |
| $CF_3SO_2$ | n-$C_4H_9$ | 4'-$ClC_6H_4$ | 1 | 3-F |
| $CF_3SO_2$ | $C_2H_5$ | $C_2H_5$ | 2 | H |
| $CF_3SO_2$ | 4'-$BrC_6H_4$ | 4'-$FC_6H_4$ | 2 | 4-$CH_3$ |
| $CF_3SO_2$ | 2'-$CH_3OC_6H_4$ | 4'-tolyl | 2 | 3-Br |
| $CF_3SO_2$ | H | H | 3 | H |
| $CF_3SO_2$ | H | $C_6H_5$ | 3 | 2-$CF_3$ |
| $CF_3SO_2$ | 4'-$ClC_6H_4$ | 4'-$CF_3C_6H_4$ | 3 | 3-$NO_2$ |

EXAMPLE III

To 4.48 g. (0.02 moles) of 2-chloro-5-trifluoromethylbenzoic acid in 10 ml. of dimethylformamide under nitrogen is added 1.05 g. (0.02 moles) of sodium meth- Employing the appropriate precursors, the compounds in the table below are prepared according to the above procedure.

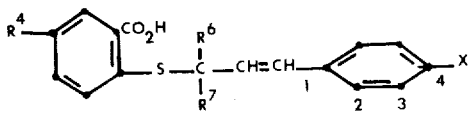

| R¹ | R⁶ | R⁷ | X |
|---|---|---|---|
| CF₃ | n-C₆H₁₃ | CH₃ | 4-CH₃ |
| CF₃SO₂ | C₆H₅ | C₆H₅ | 4-Cl |
| H | CH₃ | C₂H₅ | 3-F |
| NO₂ | p-tolyl | p-tolyl | 3-CH₃O |
| CH₃ | H | H | 2-F |
| CF₃ | n-C₃H₇ | 4'-ClC₆H₄ | 3-CF₃ |
| Br | 4'-NO₂C₆H₄ | 3'-BrC₆H₄ | 3-CF₃SO₂ |
| F | 4'-FC₆H₄ | CH₃ | 4-NO₂ |
| OCH₃ | 3'-ClC₆H₄ | 3'-CH₃OC₆H₄ | H |
| OCF₃ | 3'-CF₃C₆H₄ | 3'-CF₃SO₂C₆H₄ | 3-Br |
| (CH₃)₂NSO₂ | C₆H₅ | CH₃ | 3-CF₃ |
| (n-C₆H₁₃)₂NSO₂ | n-C₁₆H₃₃ | C₂H₅ | 3-F |
| (C₆H₅)₂NSO₂ | C₆H₅ | H | 3-CH₃O |
| (CH₃)(C₆H₅)NSO₂ | H | H | 4-NO₂ |
| [(CH₂)₅—N]SO₂ | C₂H₅ | CH₃ | 3-CF₃SO₂ |
| C₂H₅NHSO₂ | C₆H₅ | H | 3-CF₃ |
| C₆H₅NHSO₂ | C₂H₅ | CH₃ | H |
| p-CH₃C₆H₄NHSO₂ | C₆H₅ | CH₃ | 3-CH₃O |

EXAMPLE IV

To 4.5 g. (0.02 moles) of 2-chloro-5-trifluoromethylbenzoic acid contained in about 10 ml. of dimethylformamide is added 2.1 g. (0.04 moles) of sodium methoxide and a solution of 2.6 grams (0.02 moles) of α-mercaptomethylthiophene. The reaction mixture is heated with an oil bath at 90°C. for 3 hours, cooled, and added to 200 ml. of water. The resultant mixture is acidified with concentrated hydrochloric acid, and the solid which separates is isolated. The crude, dry 2-(α-thienylmethylenethio)-5-trifluoromethylbenzoic acid is dissolved in ether, and the resultant solution is treated with charcoal, filtered and concentrated. n-Hexane is added and the acid which crystallizes from solution is isolated. Yield 1.9 g.; m.p. 150°–151°C.

Recrystallization from ether - n-hexane gives 1.2 g. of acid, m.p. 152°–153°C.

Using the appropriate starting materials the following compounds are prepared according to the above procedure:

2-(β-thienylmethylenethio)-5-trifluoromethylbenzoic acid
2-(α-thienylmethylenethio)-5-chlorobenzoic acid
2-(α-thienylmethylenethio)-5-nitrobenzoic acid
2-(α-thienylmethylenethio)-5-trifluoromethoxybenzoic acid
2-(α-thienylmethylenethio)-5-trifluoromethylsulfonylbenzoic acid
2-(α-thienylmethylenethio)-5-dimethylsulfamylbenzoic acid
2-(β-thienylmethylenethio)-5-chlorobenzoic acid
2-(β-thienylmethylenethio)-5-nitrobenzoic acid
2-(β-thienylmethylenethio)-5-trifluoromethoxybenzoic acid
2-(β-thienylmethylenethio)-5-trifluoromethylsulfonylbenzoic acid
2-(β-thienylmethylenethio)-5-dimethylsulfamylbenzoic acid
2-(β-thienylmethylenethio)-5-N-methylsulfamylbenzoic acid

EXAMPLE V

Into a 1 liter, 3-necked, round bottom flask, equipped with a magnetic stirrer and reflux condenser and containing 500 ml. of N,N-dimethylformamide, is added 30.8 g. (0.10 moles) of 2-bromo-5-dimethylsulfamylbenzoic acid. To this mixture is then added 13.2 g. (0.107 moles) of benzyl mercaptan, followed by 0.32 g. (0.005 g-atom) of copper metal and 13.1 g. (0.20 moles) of potassium hydroxide. The reaction mixture is heated to 124°C. and stirred at this temperature overnight. The mixture is then cooled to room temperature and the dimethylformamide removed under reduced pressure with a rotary evaporator. The residual oil is added to 500 ml. of water and a sufficient amount of a 5 percent solution of sodium hydroxide is added to dissolve the white precipitate. The resultant alkaline solution is then extracted 3 times with diethyl ether and acidified with 6N hydrochloric acid. The crude 2-benzylthio-5-dimethylsulfamylbenzoic acid is filtered and washed with water. After several recrystallizations from acetonitrile the m.p. is 223°–225°C.

Employing the appropriate precursors, the compounds in the table below are prepared by the above procedure.

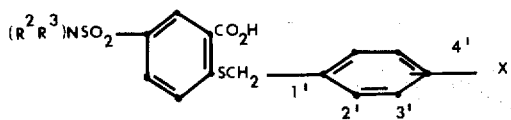

| $R^2 = R^3$ | X | M.p., °C. | Calculated C | H | Found C | H |
|---|---|---|---|---|---|---|
| $CH_3$ | 3'-methyl | 216–218 | 55.87 | 5.24 | 55.86 | 5.20 |
| $CH_3OCH_2CH_2$ | H | 142–144 | 54.65 | 5.73 | 54.86 | 5.79 |
| $CH_3CH_2CH_2CH_2$ | H | 142–144 | 60.66 | 6.71 | 60.34 | 6.67 |

The following compounds are also prepared from the appropriate precursors.

2-benzylthio-5-dimethylsulfamylbenzoic acid
2-3'-chlorobenzylthio-5-dimethylsulfamylbenzoic acid
2-4'-fluorobenzylthio-5-dimethylsulfamylbenzoic acid
2-3'-bromobenzylthio-5-dimethylsulfamylbenzoic acid
2-4'-iodobenzylthio-5-dimethylsulfamylbenzoic acid
2-4'-nitrobenzylthio-5-dimethylsulfamylbenzoic acid
2-3'-methylbenzylthio-5-dimethylsulfamylbenzoic acid
2-4'-trifluoromethylbenzylthio-5-dimethylsulfamylbenzoic acid
2-4'-trifluoromethylsulfonylbenzylthio-5-dimethylsulfamylbenzoic acid
2-benzylthio-5-di-n-hexylsulfamylbenzoic acid
2-3'-chlorobenzylthio-5-di-n-hexylsulfamylbenzoic acid
2-4'-fluorobenzylthio-5-di-n-hexylsulfamylbenzoic acid
2-3'-bromobenzylthio-5-di-n-hexylsulfamylbenzoic acid
2-4'-iodobenzylthio-5-di-n-hexylsulfamylbenzoic acid
2-4'-nitrobenzylthio-5-di-n-hexylsulfamylbenzoic acid
2-3'-methylbenzylthio-5-di-n-hexylsulfamylbenzoic acid
2-4'-trifluoromethylbenzylthio-5-di-n-hexylsulfamylbenzoic acid
2-4'-trifluoromethylsulfinylbenzylthio-5-di-n-hexylsulfamylbenzoic acid
2-benzylthio-5-di-n-butylsulfamylbenzoic acid
2-3'-chlorobenzylthio-5-di-n-butylsulfamylbenzoic acid
2-4'-fluorobenzylthio-5-di-n-butylsulfamylbenzoic acid
2-3'-bromobenzylthio-5-di-n-butylsulfamylbenzoic acid
2-4'-iodobenzylthio-5-di-n-butylsulfamylbenzoic acid
2-4'-nitrobenzylthio-5-di-n-butylsulfamylbenzoic acid
2-3'-methylbenzylthio-5-di-n-butylsulfamylbenzoic acid
2-4'-trifluoromethylbenzylthio-5-di-n-butylsulfamylbenzoic acid
2-4'-trifluoromethylsulfonylbenzylthio-5-di-n-butylsulfamylbenzoic acid
2-benzylthio-5-di(β-methoxyethyl)sulfamylbenzoic acid
2-3'-chlorobenzylthio-5-di(β-methoxyethyl)sulfamylbenzoic acid
2-4'-fluorobenzylthio-5-di(β-methoxyethyl)sulfamylbenzoic acid
2-3'-bromobenzylthio-5-di(β-methoxyethyl)sulfamylbenzoic acid
2-4'-iodobenzylthio-5-di(β-methoxyethyl)sulfamylbenzoic acid
2-4'-nitrobenzylthio-5-di(β-methoxyethyl)sulfamylbenzoic acid
2-3'-methylbenzylthio-4-di(β-methoxyethyl)sulfamylbenzoic acid
2-4'-trifluoromethylbenzylthio-4-di(β-methoxyethyl)sulfamylbenzoic acid
2-4'-trifluoromethylsulfonylbenzylthio-5-di(β-methoxyethyl)sulfamylbenzoic acid
2-3'-chlorobenzylthio-5-N-n-hexylsulfamylbenzoic acid
2-benzylthio-5-di-n-dodecylsulfamylbenzoic acid
2-3'-chlorobenzylthio-5-di-n-hexadecylsulfamylbenzoic acid
2-3'-nitrobenzylthio-5-diphenylsulfamylbenzoic acid
2-4'-trifluoromethylbenzylthio-5-N-p-tolyl-N-ethylsulfamylbenzoic acid
2-3'-bromobenzylthio-5-N-naphthyl-N-phenylsulfamylbenzoic acid
2-4'-fluorobenzylthio-5-dibenzylsulfamylbenzoic acid
2-3'-methylbenzylthio-5-di-(p-isopropylbenzyl)sulfamylbenzoic acid
2-3'-trifluoromethoxybenzylthio-5-N,N-ethylenesulfamylbenzoic acid
2-4'-iodobenzylthio-5-N,N-tetramethylenesulfamylbenzoic acid
2-3'-trifluoromethylsulfonylbenzylthio-5-N,N-pentamethylenesulfamylbenzoic acid
2-3'-chlorobenzylthio-5-N,N-(1,5'-diethylpentamethylenesulfamylbenzoic acid
2-4'-nitrobenzylthio-5-N,N-decamethylenesulfamylbenzoic acid
2-4'-bromobenzylthio-5-N,N-dodecamethylenesulfamylbenzoic acid
2-3'-trifluoromethylbenzylthio-5-N,N-(1',3',5'-tri-n-propyl)pentamethylenesulfamylbenzoic acid
2-2'-methoxybenzylthio-5-N,N-(1',8'-di-n-propyl)-nonamethylenesulfamylbenzoic acid
2-2'-chlorobenzylthio-5-N,N-(2'-methyl)tetramethylenesulfamylbenzoic acid
2-2'-methylbenzylthio-5-N,N-(2'-ethyl)pentamethylenesulfamylbenzoic acid 2-(α-naphthylmethylenethio)-5-dimethylsulfamyl-
  benzoic acid 2-(β-thienylmethylenethio)-5-N-p-tolylsulfamylben-
  zoic acid

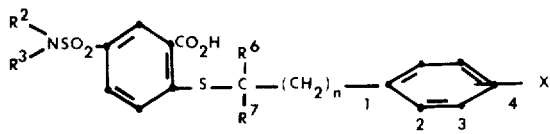

| R² | R³ | R⁶ | R⁷ | N | X |
|---|---|---|---|---|---|
| $CH_3$ | $CH_3$ | $CH_3$ | $CH_3$ | 0 | 3-Cl |
| n-$C_{12}H_{25}$ | n-$C_{12}H_{25}$ | $C_6H_5$ | $C_6H_5$ | 0 | 4-$CF_3SO_2$ |
| n-$C_{16}H_{33}$ | n-$C_{16}H_{33}$ | n-$C_6H_{13}$ | H | 1 | 2-$CH_3O$ |
| $C_6H_5$ | $C_6H_5$ | 4'-tolyl | 4'-tolyl | 1 | 3-F |
| $CH_3OC_2H_5$ | $CH_3OC_2H_5$ | 3'-$CF_3C_6H_4$ | 3'-$CF_3C_6H_4$ | 1 | 3-I |
| $C_6H_5CH_2$ | $C_6H_5CH_2$ | n-$C_3H_9$ | 4'-$ClC_6H_4$ | 2 | 2-F |
| $C_6H_5$ | $C_2H_5$ | 2'-$CH_3OC_6H_4$ | 4'-tolyl | 2 | 3-$CH_3$ |
| R² and R³ = | | | | | |
| —$CH_2CH_2$— | | H | H | 3 | 4-Br |
| —$(CH_2)_5$— | | H | $C_6H_5$ | 3 | 3-$CF_3$ |
| —$(CH_2)_{12}$— | | 4'-$ClC_6H_4$ | 4'-$CH_3OC_6H_4$ | 3 | 4-$NO_2$ |
| —$CH_2$—$CH(C_2H_5)$—$(CH_2)_3$— | | n-$C_6H_{13}$ | $C_6H_5$ | 2 | 4-Cl |

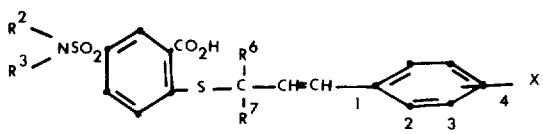

| R² | R³ | R⁶ | R⁷ | X |
|---|---|---|---|---|
| n-$C_{12}H_{25}$ | $CH_3$ | n-$C_6H_{13}$ | $CH_3$ | 4-$CH_3$ |
| n-$C_{16}H_{33}$ | $C_6H_5$ | $C_6H_5$ | $C_6H_5$ | Cl |
| $C_2H_5$ | $CH_3$ | $CH_3$ | $C_2H_5$ | Br |
| $C_6H_5CH_2$ | $C_6H_5CH_2$ | 4'-tolyl | 4'-$ClC_6H_4$ | F |
| $C_6H_5$ | $C_6H_5$ | 4'-$NO_2C_6H_4$ | 3'$FC_6H_4$ | I |
| $CH_3$ | $CH_3$ | 3'-$CH_3OC_6H_4$ | 4'-$BrC_6H_4$ | $CH_3O$ |
| R² and R³ = | | | | |
| —$CH_2CH_2$— | | 3'-$CF_3SO_2C_6H_4$ | 4'-$FC_6H_4$ | $CF_3$ |
| —$(CH_2)_4$— | | 4'-$IC_6H_4$ | 3'-$CF_3C_6H_4$ | $CF_3SO_2$ |
| —$(CH_2)_5$— | | o-tolyl | H | $NO_2$ |
| —$CH_2$—$CH(C_2H_5)$—$(CH_2)_3$ | | H | H | H |

2-(α-naphthylmethylenethio)-5-di-n-hexylsulfamyl-
  benzoic acid
2-(α-naphthylmethylenethio)-5-di-n-butylsulfamyl-
  benzoic acid
2-(β-naphthylmethylenethio)-5-di-(β-methoxye-
  thyl)sulfamylbenzoic acid
2-(β-naphthylmethylenethio)-5-di-n-dodecylsul-
  famylbenzoic acid
2-(β-naphthylmethylenethio)-5-di-n-hexadecylsul-
  famylbenzoic acid
2-(α-thienylmethylenethio)-5-diphenylsulfamylben-
  zoic acid
2-(α-thienylmethylenethio)-5-N-p-tolyl-N-ethylsul-
  famylbenzoic acid
2-(α-thienylmethylenethio)-5-dibenzylsulfamylben-
  zoic acid
2-(β-thienylmethylenethio)-5-di-(p-isopropylben-
  zyl)sulfamylbenzoic acid
2-(β-thienylmethylenethio)-5-N,N-pentame-
  thylenesulfamylbenzoic acid
2-(β-thienylmethylenethio)-5-N,N-(2'-methyl)tet-
  ramethylenesulfamylbenzoic acid
2-(β-thienylmethylenethio)-5-N-phenylsulfamylben-
  zoic acid

EXAMPLE VI

To 100 ml. of N,N-dimethylformamide is added 200 mg. of copper powder, 7.9 g. (0.12 moles) of potassium hydroxide, 7.5 g. (0.06 moles) of benzyl mercaptan and 19 g. (0.06 moles) of 3-iodo-5-trifluoromethylbenzoic acid. The mixture is heated under a nitrogen atmosphere for 18 hours at 140°C. The dimethylformamide is evaporated under reduced pressure and 200 ml. of water is added to the residue. The mixture is filtered and the filtrate is acidified with concentrated hydrochloric acid. The 3-benzylthio-5-trifluoromethylbenzoic acid that precipitates is filtered and recrystallized from chloroform-n-hexane, m.p. 127°–130°C.; yield 16.5 g. After sublimation at 200°C./0.02 mm and recrystallization from ether-n-hexane, the m.p. is 135°–136.5°C.

| Anal. | Calc'd. for $C_{15}H_{11}O_2F_3S$: | C, 57.68; H, 3.55. |
|---|---|---|
| | Found: | C, 58.04; H, 3.60. |

The following compounds are also prepared by the above procedure:

3-2'-methylbenzylthio-5-trifluoromethylbenzoic acid
3-3'-trifluoromethylbenzylthio-5-trifluoromethylbenzoic acid
3-4'-chlorobenzylthio-5-trifluoromethylbenzoic acid
3-3'-nitrobenzylthio-5-trifluoromethylbenzoic acid
3-benzylthio-5-nitrobenzoic acid
3-2'-methylbenzylthio-5-nitrobenzoic acid
3-3'-trifluoromethylbenzylthio-5-nitrobenzoic acid
3-4'-bromobenzylthio-5-nitrobenzoic acid
3-2'-methoxybenzylthio-5-nitrobenzoic acid
3-benzylthio-5-trifluoromethoxybenzoic acid
3-2'-methylbenzylthio-5-trifluoromethoxybenzoic acid
3-4'-trifluoromethylsulfonylbenzylthio-5-trifluoromethoxybenzoic acid
3-2'-fluorobenzylthio-5-trifluoromethoxybenzoic acid
3-3'-iodobenzylthio-5-trifluoromethoxybenzoic acid
2-3'-chlorobenzylthio-5-N-n-hexylsulfamylbenzoic acid
3-benzylthio-5-trifluoromethylsulfonylbenzoic acid
3-3'-chlorobenzylthio-5-trifluoromethylsulfonylbenzoic acid
3-2'-fluorobenzylthio 5-trifluoromethylsulfonylbenzoic acid
3-4'-nitrobenzylthio-5-trifluoromethylsulfonylbenzoic acid
3-3'-trifluoromethylbenzylthio-5-trifluoromethylsulfonylbenzoic acid
3-benzylthio-5-dimethylsulfamylbenzoic acid
3-3'-bromobenzylthio-5-dimethylsulfamylbenzoic acid
3-4'-trifluoromethylbenzylthio-5-dimethylsulfamylbenzoic acid
3-4'-methylbenzylthio-5-dimethylsulfamylbenzoic acid
3-3'-nitrobenzylthio-5-dimethylsulfamylbenzoic acid
3-benzylthio-5-di-n-butylsulfamylbenzoic acid
3-3'-bromobenzylthio-5-di-n-butylsulfamylbenzoic acid
3-4'-trifluoromethylbenzylthio-5-di-n-butylsulfamylbenzoic acid
3-4'-methylbenzylthio-5-di-n-butylsulfamylbenzoic acid
3-3'-nitrobenzylthio-5-di-n-butylsulfamylbenzoic acid
3-($\alpha$-naphthylmethylenethio)-5-trifluoromethylbenzoic acid
3-($\alpha$-naphthylmethylenethio)-5-nitrobenzoic acid
3-($\alpha$-naphthylmethylenethio)-5-trifluoromethoxybenzoic acid
3-($\alpha$-naphthylmethylenethio)-5-trifluoromethylsulfonylbenzoic acid
3-($\beta$-naphthylmethylenethio)-5-dimethylsulfamylbenzoic acid
3-($\alpha$-thienylmethylenethio)-5-di-n-butylsulfamylbenzoic acid
3-($\beta$-thienylmethylenethio)-5-diphenylsulfamylbenzoic acid
3-(3'-bromobenzylthio)-5-diphenylsulfamylbenzoic acid
3-benzylthio-5-dibenzylsulfamylbenzoic acid
3-(4'-trifluoromethylbenzylthio)-5-N-phenyl-N-ethylsulfamylbenzoic acid
3-(3'-methylbenzylthio)-5-N,N-tetramethylenesulfamylbenzoic acid
3-(4'-nitrobenzylthio)-5-N,N-(2'-ethyl)pentamethylenesulfamylbenzoic acid
3-(4'-fluorobenzylthio)-5-di-n-hexadecylsulfamylbenzoic acid
3-(3'-chlorobenzylthio)-5-N-n-butylsulfamylbenzoic acid
3-(2'-fluorobenzylthio)-5-N-phenylsulfamylbenzoic acid

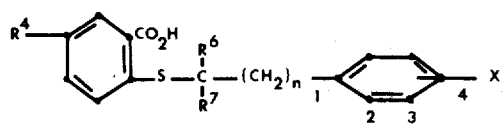

| $R^4$ | $R^6$ | $R^7$ | n | X |
|---|---|---|---|---|
| $NO_2$ | $n\text{-}C_6H_{13}$ | H | 0 | 3-Cl |
| $NO_2$ | 4'-tolyl | $C_2H_5$ | 1 | 3-Br |
| $NO_2$ | $C_6H_5$ | $C_6H_5$ | 2 | 4-I |
| $CF_3$ | 4'-tolyl | 4'-tolyl | 1 | 2-$OCH_3$ |
| $CF_3$ | 3'-$BrC_6H_4$ | 2'-$CH_3OC_6H_4$ | 2 | 2-F |
| $CF_3$ | $C_2H_5$ | $C_2H_5$ | 3 | 3-$CF_3$ |
| $CF_3O$ | $CH_3$ | H | 0 | 4-$CH_3$ |
| $CF_3O$ | H | H | 2 | 3-$CF_3SO_2$ |
| $CF_3O$ | H | H | 2 | H |
| $CF_3SO_2$ | $C_6H_5$ | $CH_3$ | 3 | 4-$NO_2$ |
| $CF_3SO_2$ | 4'-$FC_6H_4$ | 3'-$ClC_6H_4$ | 3 | 2-Cl |
| $CF_3SO_2$ | 3'-$CF_3C_6H_4$ | 2'-$CH_3C_6H_4$ | 1 | 3-$NO_2$ |
| $(CH_3)_2NSO_2$ | H | H | 2 | 4-$CF_3$ |
| $(n\text{-}C_{16}H_{33})_2NSO_2$ | $CH_3$ | $CH_3$ | 3 | 4-Br |
| $(C_6H_5)_2NSO_2$ | $CH_3$ | $C_2H_5$ | 3 | 3-$CH_3$ |
| $(CH_2)_5\text{—}NSO_2$ | 3'-$CF_3SO_2C_6H_4$ | H | 0 | 3-$OCH_3$ |
| $(C_6H_5)(C_2H_5)NSO_2$ | 4'-$IC_6H_4$ | $C_6H_5$ | 1 | 4-F |
| $(C_6H_5CH_2)_2NSO_2$ | $CH_3$ | $n\text{-}C_6H_{13}$ | 2 | 4-$CF_3SO_2$ |
| $C_2H_5NHSO_2$ | $CH_3$ | $C_6H_5$ | 2 | H |
| $C_6H_5NHSO_2$ | H | H | 1 | 3-Cl |
| $p\text{-}CH_3C_6H_4NHSO_2$ | $C_2H_5$ | $C_2H_5$ | 0 | 3-$CF_3$ |

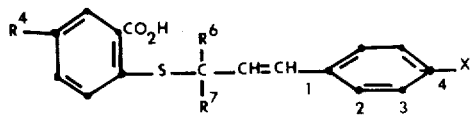

| R⁴ | R⁶ | R⁷ | X |
|---|---|---|---|
| NO₂ | H | H | H |
| NO₂ | n-C₂H₁₃ | n-C₆H₁₃ | 3-Cl |
| CF₃ | 3'-FC₆H₄ | H | 4-Br |
| CF₃ | C₆H₅ | C₆H₅ | 2-F |
| CF₃O | 4'-ClC₆H₄ | 4'-C₆H₄ | 4-I |
| CF₃O | 4'-tolyl | 4'-tolyl | 3-CF₃ |
| CF₃SO₂ | 3'-CF₃C₆H₄ | 3'-BrC₆H₄ | 2-OCH₃ |
| CF₃SO₂ | 4'-IC₆H₄ | 4'-CH₃OC₆H₄ | 3-CH₃ |
| (CH₃)₂NSO₂ | H | H | 3-NO₂ |
| (n-C₁₆H₃₃)₂NSO₂ | 3'-NO₂C₆H₄ | H | 3-NO₂ |
| (C₆H₅)₂NSO₂ | 4'-CF₃SO₂C₆H₄ | 3'-tolyl | 4-CF₃SO₂ |
| (CH₃)(C₂H₅)NSO₂ | H | C₂H₅ | 3-CF₃ |
| ⎕(CH₂)₄—NSO₂ | n-C₃H₇ | n-C₄H₉ | 4-Cl |
| n-C₃H₇NHSO₂ | H | H | H |
| C₆H₅NHSO₂ | C₆H₅ | CH₃ | 3-Cl |
| C₆H₅CH₂NHSO₂ | C₂H₅ | CH₃ | 3-CF₃ |

EXAMPLE VII

To a solution of 4.15 g. (0.030 moles) of potassium carbonate in 50 ml. of water is successively added 100 ml. of ethanol, 5.05 g. (0.030 moles) of 5-methyl-2-mercaptobenzoic acid, and 3.8 g. (0.030 moles) of benzyl chloride. After the evolution of carbon dioxide ceases (about 10 minutes), the mixture is refluxed on a steam bath for one hour. The mixture is cooled, and the major portion of the solvent is evaporated under reduced pressure. The cloudy, white liquid residue is diluted to a volume of about 600 ml. with water. The mixture is filtered, cooled, and acidified with 6 N hydrochloric acid. The white precipitate which forms is separated, filtered, and triturated with about 400 ml. of water. Filtration and drying under high vacuum provides 6.9 g. (89 percent yield) of 2-benzylthio-5-methylbenzoic acid, m.p. 169°–171°C. sint. 167°C.

The following compounds are similarly obtained:

| | m.p.,°C. |
|---|---|
| 2-3'-nitrobenzylthio-5-methylbenzoic acid | 164–167° sint. 162 |
| 2-3'-trifluoromethylbenzylthio-5-methylbenzoic acid | 153–155 |
| 2-4'-chlorobenzylthio-5-methylbenzoic acid | 188–191 |
| 2-benzylthio-4-trifluoromethylbenzoic acid | 157–158.5 |
| 2-α-methylbenzylthio-5-chlorobenzoic acid | 153–154 |
| 2-(α-thienylmethylenethio)-5-chlorobenzoic acid | 154–156 |
| 2-(β-thienylmethylenethio)-5-chlorobenzoic acid | 165–167 |
| 2-(cinnamylthio)-5-chlorobenzoic acid | 179–180.5 |

The following compounds are also prepared from the appropriate reagents by the above procedure.
2-benzylthiobenzoic acid
2-3'-fluorobenzylthio-5-methylbenzoic acid
2-4'-trifluoromethylbenzylthio-5-methylbenzoic acid
2-3'-methylbenzylthio-5-chlorobenzoic acid
2-2'-methoxybenzylthio-5-chlorobenzoic acid
2-4'-trifluoromethylsulfonylbenzylthio-5-methylbenzoic acid
2-4'-chlorobenzylthio-5-bromobenzoic acid
2-3'-bromobenzylthio-5-bromobenzoic acid
2-2'-fluorobenzylthio-5-fluorobenzoic acid
2-4'-methoxybenzylthio-5-fluorobenzoic acid
2-3'-trifluoromethylbenzylthio-5-trifluoromethylbenzoic acid
2-4'-nitrobenzylthio-5-trifluoromethylbenzoic acid
2-3'-iodobenzylthio-5-methoxybenzoic acid
2-3'-trifluoromethylbenzylthio-5-trifluoromethylsulfonylbenzoic acid
2-3'-nitrobenzylthio-5-nitrobenzoic acid
2-3'-trifluoromethylsulfonylbenzylthio-5-trifluoromethoxybenzoic acid
2-4'-methylbenzylthio-5-di-n-hexylsulfamylbenzoic acid
2-3'-fluorobenzylthio-4-methylbenzoic acid
2-4'-trifluoromethylbenzylthio-4-methylbenzoic acid
2-3'-methylbenzylthio-4-chlorobenzoic acid
2-2'-methoxybenzylthio-4-chlorobenzoic acid
2-4'-trifluoromethylsulfonylbenzylthio-4-methylbenzoic acid
2-4'-chlorobenzylthio-4-bromobenzoic acid
2-3'-bromobenzylthio-4-bromobenzoic acid
2-2'-fluorobenzylthio-4-fluorobenzoic acid
2-4'-methoxybenzylthio-4-fluorobenzoic acid
2-3'-trifluoromethylbenzylthio-4-trifluoromethylbenzoic acid
2-4'-nitrobenzylthio-4-trifluoromethylbenzoic acid
2-3'-iodobenzylthio-4-methoxybenzoic acid
2-3'-trifluoromethylbenzylthio-4-trifluoromethylsulfonylbenzoic acid
2-3'-nitrobenzylthio-4-nitrobenzoic acid
2-3'-trifluoromethylsulfonylbenzylthio-4-trifluoromethoxybenzoic acid
2-4'-methylbenzylthio-4-di-n-hexylsulfamylbenzoic acid
3-3'-methylbenzylthiobenzoic acid
3-4'-chlorobenzylthiobenzoic acid
3-3'-fluorobenzylthio-5-methylbenzoic acid
3-4'-trifluoromethylbenzylthio-5-methylbenzoic acid
3-3'-methylbenzylthio-5-chlorobenzoic acid
3-2'-methoxybenzylthio-5-chlorobenzoic acid
3-4'-trifluoromethylsulfonylbenzylthio-5-methylbenzoic acid
3-4'-chlorobenzylthio-5-bromobenzoic acid
3-3'-bromobenzylthio-5-bromobenzoic acid
3-2'-fluorobenzylthio-5-fluorobenzoic acid
3-4'-methoxybenzylthio-5-fluorobenzoic acid
3-3'-trifluoromethylbenzylthio-5-trifluoromethylbenzoic acid
3-4'-nitrobenzylthio-5-trifluoromethylbenzoic acid
3-3'-iodobenzylthio-5-methoxybenzoic acid
3-3'-trifluoromethylbenzylthio-5-trifluoromethylsulfonylbenzoic acid
3-3'-nitrobenzylthio-5-nitrobenzoic acid
3-3'-trifluoromethylsulfonylbenzylthio-5-trifluoromethoxybenzoic acid
3-4'-methylbenzylthio-5-di-n-hexylsulfamylbenzoic acid
4-3'-fluorobenzylthio-3-methylbenzoic acid 4-4'-trifluoromethylbenzylthio-3-methylbenzoic acid
4-3'-methylbenzylthio-3-chlorobenzoic acid
4-2'-methoxybenzylthio-3-chlorobenzoic acid
4-4'-trifluoromethylsulfonylbenzylthio-3-chlorobenzoic acid
4-4'-chlorobenzylthio-3-bromobenzoic acid
4-3'-bromobenzylthio-3-bromobenzoic acid
4-2'-fluorobenzylthio-3-fluorobenzoic acid
4-4'-methoxybenzylthio-3-fluorobenzoic acid
4-3'-trifluoromethylbenzylthio-3-trifluoromethylbenzoic acid
4-4'-nitrobenzylthio-3-trifluoromethylbenzoic acid
4-3'-iodobenzylthio-3-methoxybenzoic acid
4-3'-trifluoromethylbenzylthio-3-trifluoromethylsulfonylbenzoic acid
4-3'-nitrobenzylthio-3-nitrobenzoic acid
4-3'-trifluoromethylsulfonylbenzylthio-3-trifluoromethoxybenzoic acid
4-4'-methylbenzylthio-3-di-n-hexylsulfamylbenzoic acid
2-(α-naphthylmethylenethio)-5-methylbenzoic acid
2-(β-naphthylmethylenethio)-5-trifluoromethylbenzoic acid
2-(α-naphthylmethylenethio)-4-nitrobenzoic acid
3-(α-thienylmethylenethio)-5-methylbenzoic acid
4-(α-thienylmethylenethio)-3-chlorobenzoic acid
2-(β-thienylmethylenethio)-4-bromobenzoic acid
2-3'-bromobenzylthio-5-di-n-hexadecylsulfamylbenzoic acid
2-benzylthio-5-diphenylsulfamylbenzoic acid
2-4'-trifluoromethylbenzylthio-5-dibenzylsulfamylbenzoic acid
2-4'-methylbenzylthio-5-methylsulfamylbenzoic acid
2-2'-methoxybenzylthio-5-N-phenyl-N-ethylsulfamylbenzoic acid
2-3'-chlorobenzylthio-5-N,N-pentamethylenesulfamylbenzoic acid
2-2'-fluorobenzylthio-5-N,N-dodecamethylenesulfamylbenzoic acid
2-4'-iodobenzylthio-5-N-methyl-N-ethylsulfamylbenzoic acid
2-3'-trifluoromethylsulfonylbenzylthio-5-N-benzyl-N-phenylsulfamylbenzoic acid
2-4'-nitrobenzylthio-5-di-α-naphthylsulfamylbenzoic acid
2-3'-bromobenzylthio-4-di-n-hexadecylsulfamylbenzoic acid
2-benzylthio-4-diphenylsulfamylbenzoic acid
2-4'-trifluoromethylbenzylthio-4-dibenzylsulfamylbenzoic acid
2-4'-methylbenzylthio-4-methylsulfamylbenzoic acid
2-2'-methoxybenzylthio-4-N-phenyl-N-ethylsulfamylbenzoic acid
2-3'-chlorobenzylthio-4-N,N-pentamethylenesulfamylbenzoic acid
2-2'-fluorobenzylthio-4-N,N-dodecamethylenesulfamylbenzoic acid
2-4'-iodobenzylthio-4-N-methyl-N-ethylsulfamylbenzoic acid
2-3'-trifluoromethylsulfonylbenzylthio-4-N-benzyl-N-phenylsulfamylbenzoic acid
2-4'-nitrobenzylthio-4-di-α-naphthylsulfamylbenzoic acid
2-3'-chlorobenzylthio-4-N-n-propylsulfamylbenzoic acid
2-4'-fluorobenzylthio-4-N-benzylsulfamylbenzoic acid
2-2'-methoxybenzylthio-4-N-phenylsulfamylbenzoic acid
3-3'-bromobenzylthio-5-di-n-hexadecylsulfamylbenzoic acid
3-benzylthio-5-diphenylsulfamylbenzoic acid
3-4'-trifluoromethylbenzylthio-5-dibenzylsulfamylbenzoic acid
3-4'-methylbenzylthio-5-methylsulfamylbenzoic acid
3-2'-methoxybenzylthio-5-N-phenyl-N-ethylsulfamylbenzoic acid
3-3'-chlorobenzylthio-5-N,N-pentamethylenesulfamylbenzoic acid
3-2'-fluorobenzylthio-5-N,N-dodecamethylenesulfamylbenzoic acid
3-4'-iodobenzylthio-5-N-methyl-N-ethylsulfamylbenzoic acid
3-3'-trifluoromethylsulfonylbenzylthio-5-N-benzyl-N-phenylsulfamylbenzoic acid
3-4'-nitrobenzylthio-5-di-α-naphthylsulfamylbenzoic acid
4-3'-bromobenzylthio-3-di-n-hexadecylsulfamylbenzoic acid
4-benzylthio-3-diphenylsulfamylbenzoic acid
4-4'-trifluoromethylbenzylthio-3-dibenzylsulfamylbenzoic acid
4-4'-methylbenzylthio-3-methylsulfamylbenzoic acid
4-2'-methoxybenzylthio-3-N-phenyl-N-ethylsulfamylbenzoic acid
4-3'-chlorobenzylthio-3-N,N-pentamethylenesulfamylbenzoic acid
4-2'-fluorobenzylthio-3-N,N-dodecamethylenesulfamylbenzoic acid
4-4'-iodobenzylthio-3-N-methyl-N-ethylsulfamylbenzoic acid
4-3'-trifluoromethylsulfonylbenzylthio--N-benzyl-N-phenylsulfamylbenzoic -N-phenylsulfamylbenzoic acid
4-4'-nitrobenzylthio-3-di-α-naphthylsulfamylbenzoic acid

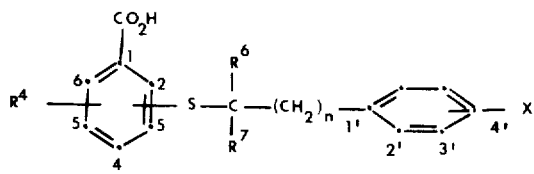

| Position and Identity of $R^4$ | Position of Arylalkylthio Group | $R^6$ | $R^7$ | n | X |
|---|---|---|---|---|---|
| 5-$CH_3$ | 2 | n-$C_6H_{13}$ | $CH_3$ | 0 | H |
| 5-Br | 2 | $C_6H_5$ | $CH_3$ | 1 | 3'-Br |
| 5-F | 2 | n-$C_6H_{13}$ | n-$C_6H_{13}$ | 2 | 3'-$CF_3$ |
| 4-Cl | 2 | $C_6H_5$ | $C_6H_5$ | 1 | 4'-$CF_3SO_2$ |
| 4-$CF_3$ | 2 | 4'-Br$C_6H_4$ | 3'-$CF_3C_6H_4$ | 3 | 4'-I |
| 4-$CH_3O$ | 2 | 4'-I$C_6H_4$ | 2'-F$C_6H_4$ | 2 | 2'-F |
| 5-$NO_2$ | 3 | 3'-Cl$C_6H_4$ | 3'-$CH_3OC_6H_4$ | 1 | 2'-$CH_3O$ |
| 5-$CF_3O$ | 3 | 4'-$CF_3SO_2C_6H_4$ | 4'-$CH_3C_6H_4$ | 2 | 3'-$NO_2$ |
| 5-$(C_2H_5)_2NSO_2$ | 3 | 3'-$NO_2C_6H_4$ | $C_6H_5$ | 3 | 4'-$CH_3$ |
| 4-$(CH_2)_5$-$NSO_2$ | 3 | $C_6H_5$ | $C_6H_5$ | 0 | 3'-Cl |
| 4-(n-$C_{16}H_{33}$)$_2NSO_2$ | 3 | H | H | 2 | 4'-$CF_3$ |
| 4-($C_6H_5$)($C_2H_5$)$NSO_2$ | 3 | $C_6H_5$ | H | 3 | H |
| 4-$C_6H_5NHSO_2$ | 3 | $C_6H_5$ | H | 3 | 3'-Cl |

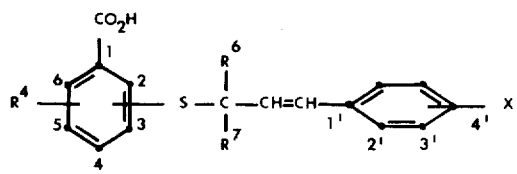

| Position and Identity of $R^4$ | Position of Cinnamylthio Group | $R^6$ | $R^7$ | X |
|---|---|---|---|---|
| 5-$CF_3$ | 2 | n-$C_6H_{13}$ | H | H |
| 5-$CF_3SO_2$ | 2 | $C_6H_5$ | $C_6H_5$ | 3'-$CF_3$ |
| 4-$NO_2$ | 2 | $CH_3$ | $CH_3$ | 4'-I |
| 5-Cl | 3 | 4'-Br$C_6H_4$ | 3'-F$C_6H_4$ | 4'-Br |
| 5-(n-$C_{16}H_{33}$)$_2NSO_2$ | 3 | H | 4'-$CF_3C_6H_4$ | 3'-Cl |
| 4-$(CH_2)_5$-$NSO_2$ | 3 | n-$C_6H_{13}$ | n-$C_6H_{13}$ | 3'-$NO_2$ |
| 4-$(C_6H_5)_2NSO_2$ | 3 | $C_2H_5$ | H | 2'-$CH_3O$ |
| 4-$C_2H_5NHSO_2$ | 3 | $CH_3$ | H | 2'-F |

EXAMPLE VIII

The benzylsulfinylbenzoic acids are prepared by treating 1 mole of the corresponding benzylthiobenzoic acid with 1 mole of hydrogen peroxide (as a 30 percent solution) in either glacial acetic acid or formic acid. Generally the reaction is heated at about 100°C. (steam bath) until all the hydrogen peroxide is consumed (the presence of hydrogen peroxide is determined with starch-iodide paper).

The reaction mixture is diluted with water and the benzylsulfinylbenzoic acid is isolated and recrystallized from a suitable solvent.

Using this procedure, the following compounds were obtained from the corresponding benzylthiobenzoic acids.

| Compound | M.p.,°C. | Elemental Analysis Calculated | | Found | |
|---|---|---|---|---|---|
| | | C | H | C | H |
| 3-benzylsulfinylbenzoic acid | 178.5–180 | 64.61 | 4.65 | 64.88 | 4.74 |
| 3-benzylsulfinyl-5-trifluoro-methylbenzoic acid | 157–158.5 | 54.87 | 3.38 | 54.94 | 3.38 |
| 2-4'-chlorobenzylsulfinyl-5-chlorobenzoic acid | 198 | 51.08 | 3.06 | 51.40 | 3.22 |
| 2-benzylsulfinyl-5-trifluoromethylbenzoic acid | 193–194 | — | — | — | — |
| 2-benzylsulfinyl-5-dimethyl-sulfamylbenzoic acid | 173–174 | 52.30 | 4.66 | 52.33 | 4.68 |

-continued

| Compound | M.p.,°C. | Elemental Analysis | | | |
| --- | --- | --- | --- | --- | --- |
| | | Calculated | | Found | |
| | | C | H | C | H |
| 2-benzylsulfinyl-5-di(β-methoxyethyl)sulfamyl benzoic acid | 127–130 | 52.73 | 5.53 | 52.73 | 4.57 |
| 2-benzylsulfinyl-5-di-n-butylsulfamylbenzoic acid | 171–174 | 58.51 | 6.47 | 58.21 | 6.45 |
| 2-benzylsulfinylbenzoic acid | 161–162 | 64.59 | 4.65 | 64.67 | 4.79 |
| 2-(α-naphthylmethylenesulfinyl)-5-trifluoromethylbenzoic acid | 178–179 | 60.31 | 3.47 | 60.22 | 3.55 |

Using the above procedure the following substituted benzylsulfinylbenzoic acids are also prepared.
3-benzylsulfinylbenzoic acid
4-benzylsulfinylbenzoic acid
2-benzylsulfinyl-5-methylbenzoic acid
2-3'-fluorobenzylsulfinyl-5-methylbenzoic acid
2-4'-chlorobenzylsulfinyl-5-methylbenzoic acid
2-3'-methylbenzylsulfinyl-5-methylbenzoic acid
3-3'-trifluoromethylbenzylsulfinyl-5-methylbenzoic acid
3-4'-nitrobenzylsulfinyl-5-methylbenzoic acid
3-2'-methoxybenzylsulfinyl-5-methylbenzoic acid
2-4'-methylbenzylsulfinyl-5-trifluoromethylbenzoic acid
2-3'-methoxybenzylsulfinyl-5-trifluoromethylbenzoic acid
2-4'-bromobenzylsulfinyl-5-trifluoromethylbenzoic acid
2-3'-trifluoromethylsulfonylbenzylsulfinyl-5-trifluoromethylbenzoic acid
3-benzylsulfinyl-5-nitrobenzoic acid
3-2'-methylbenzylsulfinyl-5-nitrobenzoic acid
3-3'-trifluoromethylbenzylsulfinyl-5-nitrobenzoic acid
3-4'-bromobenzylsulfinyl-5-nitrobenzoic acid
3-2'-methoxybenzylsulfinyl-5-nitrobenzoic acid
2-3'-methoxybenzylsulfinyl-5-chlorobenzoic acid
2-4'-chlorobenzylsulfinyl-5-chlorobenzoic acid
2-3'-trifluoromethylbenzylsulfinyl-5-chlorobenzoic acid
2-4'-trifluoromethylsulfonylbenzylsulfinyl-5-bromobenzoic acid
2-3'-methylbenzylsulfinyl-5-bromobenzoic acid
2-benzylsulfinyl-5-fluorobenzoic acid
2-3'-nitrobenzylsulfinyl-5-fluorobenzoic acid
4-3'-methylbenzylsulfinyl-3-methoxybenzoic acid
4-2'-methoxybenzylsulfinyl-3-methoxybenzoic acid
4-4'-chlorobenzylsulfinyl-3-methoxybenzoic acid
4-3'-trifluoromethylbenzylsulfinyl-3-methoxybenzoic acid
3-benzylsulfinyl-5-trifluoromethoxybenzoic acid
3-4'-methylbenzylsulfinyl-5-trifluoromethoxybenzoic acid
3-4'-trifluoromethylsulfonylbenzylsulfinyl-5-trifluoromethoxybenzoic acid
3-4'-nitrobenzylsulfinyl-5-trifluoromethylsulfonylbenzoic acid
3-3'-bromobenzylsulfinyl-5-trifluoromethylsulfonylbenzoic acid
3-2'-methoxybenzylsulfinyl-5-trifluoromethylsulfonylbenzoic acid
3-4'-iodobenzylsulfinyl-5-trifluoromethylsulfonylbenzoic acid
2-benzylsulfinyl-5-dimethylsulfamylbenzoic acid
2-3'-trifluoromethylbenzylsulfinyl-5-dimethylsulfamylbenzoic acid
2-3'-methylbenzylsulfinyl-5-di-n-hexylsulfamylbenzoic acid
2-4'-chlorobenzylsulfinyl-5-di-n-hexylsulfamylbenzoic acid
2-3'-methoxybenzylsulfinyl-5-di-n-hexylsulfamylbenzoic acid
2-2'-methylbenzylsulfinyl-5-N-ethylsulfamylbenzoic acid
2-3'-fluorobenzylsulfinyl-5-N-phenylsulfamylbenzoic acid
2-4'-nitrobenzylsulfinyl-5-N-benzylsulfamylbenzoic acid
2-(α-naphthylmethylenensulfinyl)-5-methylbenzoic acid
2-(β-naphthylmethylensulfinyl)-4-methylbenzoic acid
2-(α-thienylmethylenesulfinyl)-5-methoxybenzoic acid
3-(β-thienylmethylenesulfinyl)-5-trifluoromethoxybenzoic acid
2-benzylsulfinyl-5-di-n-hexadecylsulfamylbenzoic acid
3-3'-trifluoromethylbenzylsulfinyl-5-diphenylsulfamylbenzoic acid
4-4'-chlorobenzylsulfinyl-3-dibenzylsulfamylbenzoic acid
4-2'-methoxybenzylsulfinyl-3-N-phenyl-N-ethylsulfamylbenzoic acid
2-2'-methylbenzylsulfinyl-5-N,N-ethylenesulfamylbenzoic acid
3-4'-nitrobenzylsulfinyl-5-N,N-dodecamethylenesulfamylbenzoic acid
4-2'-fluorobenzylsulfinyl-2-N,N-(2'-methyl)tetramethylenensulfamylbenzoic acid

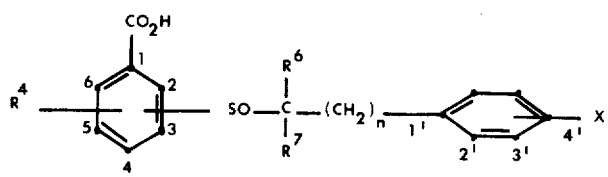

| Position and Identity of R⁴ | Position of Arylalkylsulfinyl Group | R⁶ | R⁷ | n | X |
|---|---|---|---|---|---|
| 5-CH₃ | 2 | CH₃ | CH₃ | 0 | H |
| 5-Cl | 3 | n-C₆H₁₃ | C₆H₅ | 1 | 3'-Cl |
| 3-CF₃ | 4 | H | H | 2 | 4'-Br |
| 5-CF₃SO₂ | 3 | 3'-CF₃C₆H₄ | 4'-ClC₆H₄ | 3 | 4'-F |
| 5-(CH₃OCH₂CH₂)₂NSO₂ | 3 | 4'-CF₃SO₂C₆H₄ | 2'-CH₃OC₆H₄ | 3 | 3'-I |
| 5-OCF₃ | 2 | 3'-tolyl | 3'-NO₂C₆H₄ | 2 | 3'-CF₃ |
| 5-Br | 2 | 4'-IC₆H₄ | 3'-BrC₆H₄ | 2 | 3'-CF₃SO₂ |
| 4-(n-C₁₆H₃₃)₂NSO₂ | 2 | n-C₇H₇ | C₂H₅ | 1 | 2'-CH₃O |
| 5-(CH₃)₄-NSO₂ | 3 | H | n-C₃H₉ | 1 | 2'-CH₃ |
| 4-(C₆H₅)₂NSO₂ | 2 | C₆H₅ | H | 3 | 3'-NO₂ |
| 4-p-CH₃C₆H₄NHSO₂ | 2 | C₂H₅ | H | 3 | 2'-F |

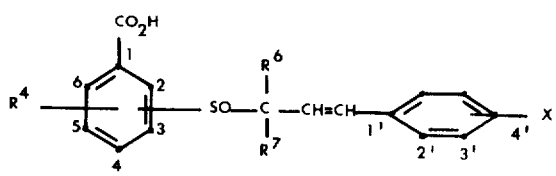

| Position and Identity of R⁴ | Position of Cinnamylsulfinyl Group | R⁶ | R⁷ | X |
|---|---|---|---|---|
| 5-CH₃ | 2 | H | H | 3'-F |
| 5-CF₃ | 3 | CH₃ | CH₃ | 4'-Br |
| 3-CF₃SO₂ | 4 | n-C₆H₁₃ | CH₃ | 3'-CF₃ |
| 4-(CH₃OCH₂CH₂)₂NSO₂ | 2 | C₆H₅ | C₆H₅ | 4'-NO₂ |
| 4-(CH₂)₄NSO₂ | 2 | 4'-tolyl | 4'-ClC₆H₄ | H |
| 5-OCF₃ | 3 | 4'-FC₆H₄ | 4'-CF₃C₆H₄ | 4'-CF₃SO₂ |

EXAMPLE IX

The benzylsulfonylbenzoic acids of the instant invention are prepared by oxidizing either the benzylsulfinylbenzoic acids or the benzylthiobenzoic acids. For convenience, we prefer to prepare these compounds by the latter procedure.

To 200 ml. of 97 percent formic acid is added 6.1 g. (0.024 moles) of 2-benzylthio-5-methylbenzoic acid. The mixture is heated on a water bath at about 54°C. while 15 ml. of 30 percent hydrogen peroxide is added over a period of about 25 minutes. After the addition of the hydrogen peroxide is complete, the mixture is heated at 54°C. for about 3 hours. The reaction mixture is cooled to room temperature and allowed to stand overnight.

The formic acid is distilled at reduced pressure and the pale yellow solid residue is dried over phosphorous pentoxide for about 2 hours. It is triturated with about 300 ml. of water, filtered, and dried in a vacuum desiccator over phosphorous pentoxide to yield 6.5 g. (91 percent yield) of 2-benzylsulfonyl-5-methylbenzoic acid, m.p. 198°–201°C.

By analogous procedures the compounds below are prepared from suitable starting materials.

| Compound | m.p., °C. | Elemental Analysis Calculated C | H | Found C | H |
|---|---|---|---|---|---|
| 2-3'-nitrobenzylsulfonyl-5-methylbenzoic acid | 213–216 | — | — | — | — |
| 2-3'-trifluoromethylbenzylsulfonyl-5-methylbenzoic acid | 156–159; sint. 151 | — | — | — | — |
| 2-4'-chlorobenzylsulfonyl-5-methylbenzoic acid | 184–186; sint. 182 | — | — | — | — |
| 2-3'-methylbenzylsulfonyl-5-nitrobenzoic acid | 244–246 | — | — | — | — |
| 2-benzylsulfonyl-5-trifluoromethylbenzoic acid | 171–172.5 | — | — | — | — |
| 2-3'-methylbenzylsulfonyl-5-dimethylsulfamyl- | 223–225 | 51.35 | 4.80 | 51.54 | 4.94 |

-continued

| Compound | m.p.,°C. | Elemental Analysis | | | |
|---|---|---|---|---|---|
| | | Calculated | | Found | |
| | | C | H | C | H |
| benzoic acid | | | | | |
| 2-3'-trifluoromethylbenzylsulfonyl-5-trifluoromethylbenzoic acid | 192–193 | 46.61 | 2.44 | 46.80 | 2.29 |
| 2-benzylsulfonyl-5-chlorobenzoic acid | 180–181.5 | 54.11 | 3.57 | 54.39 | 3.64 |
| 2-4'-chlorobenzylsulfonyl-5-chlorobenzoic acid | 184–185 | 48.71 | 2.92 | 48.44 | 2.74 |
| 3-benzylsulfonylbenzoic acid | 214–215 | 60.87 | 4.38 | 60.65 | 4.54 |
| 3-benzylsulfonyl-5-trifluoromethylbenzoic acid | 184.5–185.5 | 52.32 | 3.22 | 52.53 | 3.26 |

The compounds below are also prepared from the appropriate benzylthiobenzoic acids by means of the above procedure.

2-benzylsulfonylbenzoic acid
4-benzylsulfonylbenzoic acid
2-benzylsulfonyl-5-methylbenzoic acid
2-3'-fluorobenzylsulfonyl-5-methylbenzoic acid
2-4'-chlorobenzylsulfonyl-5-methylbenzoic acid
2-3'-methylbenzylsulfonyl-5-methylbenzoic acid
3-3'-trifluoromethylbenzylsulfonyl-5-methylbenzoic acid
3-4'-nitrobenzylsulfonyl-5-methylbenzoic acid
3-2'-methoxybenzylsulfonyl-5-methylbenzoic acid
2-4'-methylbenzylsulfonyl-5-trifluoromethylbenzoic acid
2-3'-methoxybenzylsulfonyl-5-trifluoromethylbenzoic acid
2-4'-bromobenzylsulfonyl-5-trifluoromethylbenzoic acid
2-3'-trifluoromethylsulfonylbenzylsulfonyl-5-trifluoromethylbenzoic acid
3-benzylsulfonyl-5-nitrobenzoic acid
3-2'-methylbenzylsulfonyl-5-nitrobenzoic acid
3-3'-trifluoromethylbenzylsulfonyl-5-nitrobenzoic acid
3-4'-bromobenzylsulfonyl-5-nitrobenzoic acid
3-2'-methoxybenzylsulfonyl-5-nitrobenzoic acid
2-3'-methoxybenzylsulfonyl-5-chlorobenzoic acid
2-4'-chlorobenzylsulfonyl-5-chlorobenzoic acid
2-3'-trifluoromethylbenzylsulfonyl-5-chlorobenzoic acid
2-4'-trifluoromethylsulfonylbenzylsulfonyl-5-bromobenzoic acid
2-3'-methylbenzylsulfonyl-5-bromobenzoic acid
2-benzylsulfonyl-5-fluorobenzoic acid
2-3'-nitrobenzylsulfonyl-5-fluorobenzoic acid
4-3'-methylbenzylsulfonyl-3-methoxybenzoic acid
4-2'-methoxybenzylsulfonyl-3-methoxybenzoic acid
4-4'-chlorobenzylsulfonyl-3-methoxybenzoic acid
4-3'-trifluoromethylbenzylsulfonyl-3-methoxybenzoic acid
3-benzylsulfonyl-5-trifluoromethoxybenzoic acid
3-4'-methylbenzylsulfonyl-5-trifluoromethoxybenzoic acid
3-4'-trifluoromethylsulfonylbenzylsulfonyl-5-trifluoromethoxybenzoic acid
3-4'-nitrobenzylsulfonyl-5-trifluoromethylsulfonylbenzoic acid
3-3'-bromobenzylsulfonyl-5-trifluoromethylsulfonylbenzoic acid
3-2'-methoxybenzylsulfonyl-5-trifluoromethylsulfonylbenzoic acid
3-4'-iodobenzylsulfonyl-5-trifluoromethylsulfonylbenzoic acid
2-benzylsulfonyl-5-dimethylsulfamylbenzoic acid
2-3'-trifluoromethylbenzylsulfonyl-5-dimethylsulfamylbenzoic acid
2-3'-methylbenzylsulfonyl-5-di-n-hexylsulfamylbenzoic acid
2-4'-chlorobenzylsulfonyl-5-di-n-hexylsulfamylbenzoic acid
2-3'-methoxybenzylsulfonyl-5-di-n-hexylsulfamylbenzoic acid
2-2'-methylbenzylsulfonyl-5-N-ethylsulfamylbenzoic acid
2-3'-fluorobenzylsulfonyl-5-phenylsulfamylbenzoic acid
2-4'-nitrobenzylsulfonyl-5-N-benzylsulfamylbenzoic acid
2-(α-naphthylmethylenesulfonyl)-5-methylbenzoic acid
2-(β-naphthylmethylenensulfonyl)-4-methylbenzoic acid
2-(α-thienylmethylenesulfonyl)-5-methoxybenzoic acid
3-(β-thienylmethylenesulfonyl)-5-trifluoromethoxybenzoic acid
2-benzylsulfonyl-5-di-n-hexadecylsulfamylbenzoic acid
3-3'-trifluoromethylbenzylsulfonyl-5-diphenylsulfamylbenzoic acid
4-4'-chlorobenzylsulfonyl-3-dibenzylsulfamylbenzoic acid
4-2'-methoxybenzylsulfonyl-3-N-phenyl-N-ethylsulfamylbenzoic acid
2-2'-methylbenzylsulfonyl-5-N,N-ethylenesuylfamylbenzoic acid
3-4'-nitrobenzylsulfonyl-5-N,N-dodecamethylenesulfamylbenzoic acid
4-2'-fluorobenzylsulfonyl-2-N,N-(2'-methyl)tetramethylenesulfamylbenzoic acid

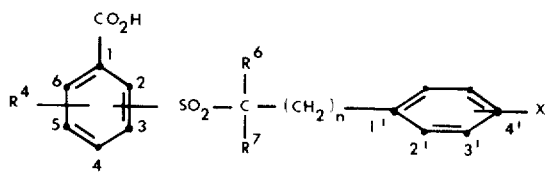

| Position and Identity of R⁴ | Position of Arylalkylsulfonyl Group | R⁶ | R⁷ | n | X |
|---|---|---|---|---|---|
| 5-CH₃ | 2 | CH₃ | CH₃ | 0 | H |
| 5-Cl | 3 | n-C₆H₁₃ | C₆H₅ | 1 | 3'-Cl |
| 3-Cl | 4 | H | H | 2 | 4'-Br |
| 5-CF₃SO₂ | 3 | 3'-CF₃C₆H₄ | 4'-ClC₆H₄ | 3 | 4'-F |
| 5-(CH₃OCH₂CH₂)₂NSO₂ | 3 | 4'-CF₃SO₂C₆H₄ | 2'-CH₃OC₆H₄ | 3 | 3'-I |
| 5-OCF₃ | 2 | 3'-tolyl | 3'-NO₂C₆H₄ | 2 | 3'-CF₃ |
| 5-Br | 2 | 4'-IC₆H₄ | 3'-BrC₆H₄ | 2 | 3'-CF₃SO₂ |
| 4-(n-C₆H₁₃)₂NSO₂ | 2 | n-C₆H₁₃ | C₂H₅ | 1 | 2'-CH₃O |
| 5-(CH₃)₃NSO₂ | 3 | H | n-C₄H₉ | 1 | 2'-CH₃ |
| 4-(C₆H₅)₂NSO₂ | 2 | C₆H₅ | H | 3 | 3'-NO₂ |
| 4-p-CH₃C₆H₄NHSO₂ | 2 | C₆H₅ | H | 3 | 2'-F |

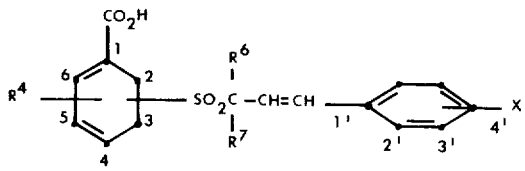

| Position and Identity of R⁴ | Position of Cinnamylsulfonyl Group | R⁶ | R⁷ | X |
|---|---|---|---|---|
| 5-CH₃ | 2 | H | H | 3'-F |
| 5-CF₃ | 3 | CH₃ | CH₃ | 4'-Br |
| 3-CF₃SO₂ | 4 | n-C₆H₁₃ | CH₃ | 3'-CF₃ |
| 4-(CH₃OCH₂CH₂)₂NSO₂ | 2 | C₆H₅ | C₆H₅ | 4'-NO₂ |
| 4-(CH₃)₃NSO₂ | 2 | 4'-tolyl | 4'-ClC₆H₄ | H |
| 5-OCF₃ | 3 | 4'-FC₆H₄ | 4'-CF₃C₆H₄ | 4'-CF₃SO₂ |

EXAMPLE X

1. Preparation of 3-Sulfino-5-trifluoromethylbenzoic Acid

To a mixture of 150 ml. of water and 250 ml. of tetrahydrofuran is added 0.10 moles of 3-amino-5-trifluoromethylbenzoic acid. The resultant solution is cooled to about 18°C. and 50 ml. of concentrated sulfuric acid is slowly added to the mixture. During the addition the temperature is kept below about 30°C. After the addition is complete, the resultant mixture is cooled to about −2°C. and a solution of 8.15 g. of sodium nitrite in about 120 ml. of water is slowly added with stirring, to the mixture over a period of about 45 minutes. During this latter addition the temperature of the mixture is kept below about 5°C.

The mixture is stirred for 15 minutes at −2°C. and then about 0.63 moles of sulfur dioxide is added over a 5 minute period. During the addition of the gas the temperature of the mixture is kept at about 0°C. 25 g. of finely divided copper is added in 2.5 g. portion about every 10 minutes over a period of 1 ½ hours. Sulfur dioxide is again passed into the mixture for about 1 hour until a total of about 1.26 moles has been added. During the above additions the temperature of the mixture is kept below 3°C. After the addition of the sulfur is complete the temperature is slowly raised to about 10°C. The reaction mixture is allowed to stand at room temperature for about 16 hours. The aqueous phase is separated from the organic layer and the latter is treated with decolorizing charcoal. It is concentrated and chloroform is added. The resultant mixture is then concentrated under reduced pressure and the resultant crystalline slurry is cooled to about 18°C. and filtered. The 3-sulfino-5-trifluoromethylbenzoic acid is washed well with chloroform and dried at about 50°C.

2. Preparation of benzyl 3-benzylsulfonyl-5-trifluoromethylbenzoate 0.50 Moles of 3-sulfino-5-trifluoromethylbenzoic acid, 1 mole of triethylamine, and 1 mole of benzyl chloride is dissolve in 1 liter of anhydrous acetonitrile, and the resulting solution refluxed for 16 hours. The solution is cooled to 8°C. and the diethylamine hydrochloride is filtered and washed with acetonitrile. The filtrate is concentrated under reduced pressure and about 600 ml. of 5 percent hydrochloric acid is added to the residue. This mixture is extracted with six ½ liter portions of ether which are combined and washed with two 0.6-liter portions of water, treated with decolorizing charcoal and concentrated to a volume of 500 ml. To this mixture is added 1 liter of n-hexane, and the resultant slurry is cooled to about 5°C. The mixture is filtered, washed with n-hexane and air-dried at room temperature to give benzyl 3-benzylsulfonyl-5-trifluoromethylbenzoate.

3. Preparation of 3-benzylsulfonyl-5-trifluoromethylbenzoic acid 0.10 moles of benzyl 3-benzylsulfonyl-5-trifluoromethylbenzoate is refluxed in a 10 percent sulfuric acid solution for 1 hour. The reaction mixture is cooled, made alkaline with sodium hydroxide and extracted with ether. The aqueous phase is acidified and extracted with ether. The ether extracts are dried over sodium sulfate and evaporated to give 3-benzylsulfonyl-5-trifluoromethylbenzoic acid, m.p. 184°–185.5°C.

Using the appropriae aminobenzoic acids, the benzylsulfonylbenzoic acids listed in Example IX are prepared according to the general procedure of this example.

EXAMPLE XI 0.10 Moles of 2-benzylthio-5-trifluoromethylbenzoic acid is added to 500 ml. of ethanol containing 3 percent hydrochloric acid. The mixture is refluxed for 3 hours, diluted with water, and made alkaline with sodium hydroxide. The alkaline solution is extracted with ether and the ether extracts are dried over anhydrous sodium sulfate and evaporated. The residue of methyl-2-benzylthio-5-trifluoromethylbenzoate is purified by distillation under reduced pressure.

The corresponding n-propyl and n-butyl esters are similarly prepared from n-propanol and n-butanol, respectively.

Using the above procedure the methyl, n-propyl and n-butyl esters of the compounds in Examples I-X are prepared.

EXAMPLE XII 0.10 Moles of methyl-2-benzylthio-5-trifluoromethylbenzoate is added to 500 ml. of an ammonia-methanol solution and the mixture stirred at room temperature for 5 hours. Upon dilution of the mixture with water, 2-benzylthio-5-trifluoromethylbenzamide separates from solution and is recovered.

The corresponding benzamides of the compounds listed in Example I-X are similarly prepared from their respective methyl esters.

EXAMPLE XIII 0.10 Moles of 2-benzylthio-5-trifluoromethylbenzoic acid is added with stirring to 500 ml. of an aqueous solution of 0.10 moles of sodium hydroxide.

After solution is complete, the resultant solution is lyophilized to give 0.10 moles of sodium 2-benzylthio-5-trifluoromethylbenzoate.

Using g-equivalent weights of the appropriate bases the following salts are similarly obtained:
  potassium 2-benzylthio-5-trifluoromethylbenzoate
  ammonium 2-benzylthio-5-trifluoromethylbenzoate
  calcium 2-benzylthio-5-trifluoromethylbenzoate
  magnesium 2-benzylthio-5-trifluoromethylbenzoate Using the above procedure, the pharmaceutically acceptable sodium, potassium, ammonium, calcium, and magnesium salts of the compounds in Examples I-X are also prepared.

EXAMPLE XIV 0.10 Moles of crude 2-benzylthio-5-trifluoromethylbenzoic acid, obtained in the procedure of Example I, is added with stirring to 1 liter of an aqueous solution of 0.05 moles of Ba(OH)$_2$.8H$_2$O. The solution is extracted with ether and lyophilized to give 0.05 moles of barium 2-benzylthio-5-trifluoromethylbenzoate.

The barium salt is then added to water, the resultant solution acidified, and the purified 2-benzylthio-5-trifluoromethylbenzoic acid which separates is isolated. The pharmaceutically acceptable salts of this acid are prepared according to the procedure of Example XIII.

Using the g-equivalent weights of the appropriate bases the following pharmaceutically unacceptable salts are similarly obtained:
  cesium 2-benzylthio-5-trifluoromethylbenzoate
  strontium 2-benzylthio-5-trifluoromethylbnezoate These salts are converted to the pharmaceutically acceptable salts listed in Example XIII according to the above procedure.

Using the above procedure the pharmaceutically unacceptable barium, strontium, and cesium salts of the compounds in Examples I-X are also prepared.

EXAMPLE XV

Three groups, each comprising 4 normal Sprague-Dawley (Charles River) male rats each weighing from 160–220 g., are fed Purina ground rat chow. One group of rats is designated as the control group and merely receives rat chow. A second group of rats is fed Purina rat chow containing 0.25 percent by weight of 2-benzylthio-5-trifluoromethylbenzoic acid, and the third group is fed rat chow containing 0.25 percent by weight of p-chlorophenoxyisobutyric acid, a standard hypolipemic agent.

The rats are fed the above products for two overnight feeding periods. On the morning of the third day they are anesthetized and bled from the abdominal aorta.

The total plasma cholesterol in the collected blood is determined by the method of J. J. Carr and I. J. Drekter reported in Clin. Chem., 2, 353 (1956).

The cholesterol level of the group of animals fed the rat chow containing the 2-benzylthio-5-trifluoromethylbenzoic acid is significantly less than that of the animals only receiving rat chow without additives, and compares favorably with the cholesterol level of rats fed on the rat chow containing the standard hypolipemic agent, p-chlorophenoxyisobutyric acid.

When the above procedure is performed with the compounds listed in Examples I-XIII, similar results are obtained.

EXAMPLE XVI

Two groups of dogs, 4 animals per group, of comparable weight, are treated as follows. One group is orally administered with their standard kennel ration a gelled capsule containing a dosage level of 50–100 mg./kg. of 2-benzylthio-5-trifluoromethylbenzoic acid twice daily, while the second group merely receives kennel ration and constitutes a control group.

The animals are treated as above for a period of two weeks. Every second day during this period they are bled and the serum cholesterol and triglyceride level is determined.

The cholesterol level is determined by the method of J. J. Carr and I. J. Drekter, Clin. Chem., 2, 353 (1956) and the triglyceride level is determined by the method of E. Van Handel and D. B. Zilversmith, J. Lab. & Clin. Med., 50, 152 (1957).

The cholesterol and triglyceride blood level of the dogs receiving 2-benzylthio-5-trifluoromethylbenzoic acid is significantly less than that of the untreated animals.

Comparable results are obtained when the procedure is performed with the compounds listed in Examples I-XIII.

What is claimed is:

1. A method for reducing blood lipid levels which comprises orally or parenterally administering to a hyperlipemic mammal an effective amount of a compound of the formula:

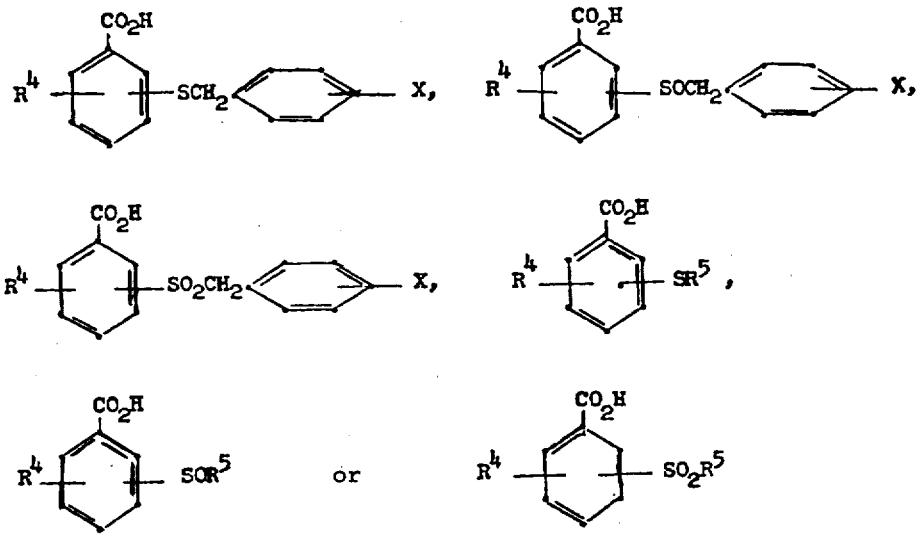

wherein
X is a member selected from the group consisting of H, —CH$_3$, CH$_3$O—, NO$_2$, Br, Cl, F, I, —CF$_3$, and CF$_3$SO$_2$—;
R$^4$ is a member selected from the group consisting of H, —CH$_3$, —CF$_3$, —NO$_2$, Cl, Br, F, -OCH$_3$, OCF$_3$ and CF$_3$SO$_2$—;
R$^5$ is a member selected from the group consisting of:

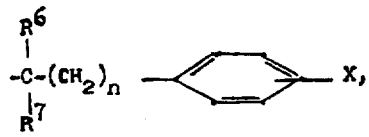

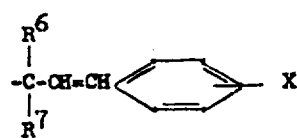

—CH$_2$-α-naphthyl and -CH$_2$-β-naphthyl;
n = 0-3;
R$^6$ and R$^7$ are members selected from the group consisting of H, lower alkyl of up to 6 carbon atoms and

provided that R$^6$ and R$^7$ are not both H when n = 0; and wherein X is as defined above;
and the salts thereof with pharmaceutically acceptable bases.

2. The method of claim 1 where the compound is:

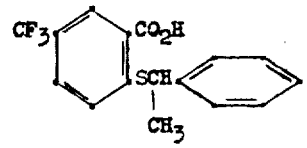

3. The method of claim 1 where the compound is:

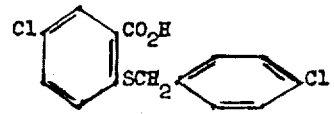

4. The method of claim 1 where the compound is:

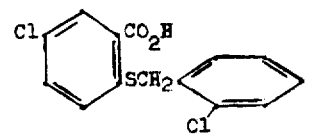

5. The method of claim 1 where the compound is:

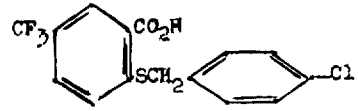

6. The method of claim 1 where the compound is:

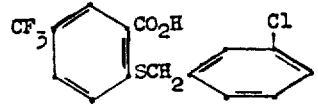

7. The method of claim 1 where the compound is:

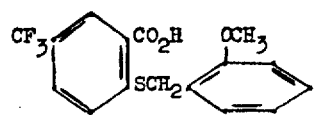

8. The method of claim 1 where the compound is:

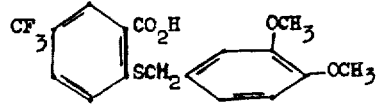

9. The method of claim 1 where the compound is:
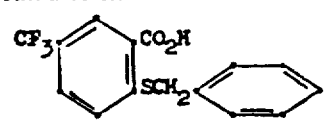
10. The method for reducing blood lipid levels which comprises orally or parenterally administering to a hyperlipemic mammal an effective amount of a compound of the formula:
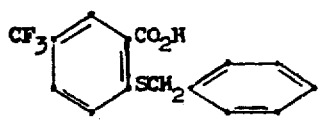 , 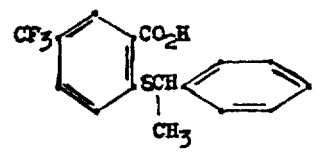 ,
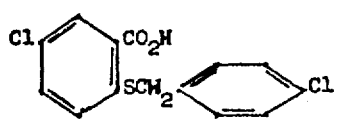 , 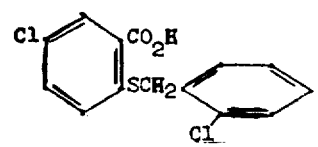 ,
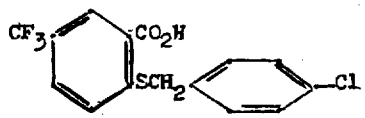 , 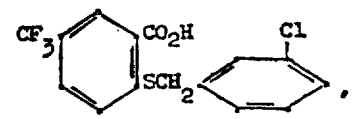 ,
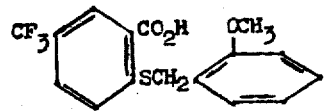 or 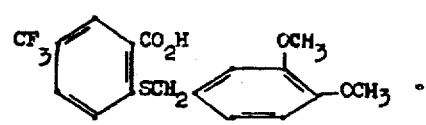 .
* * * * *

UNITED STATES PATENT AND TRADEMARK OFFICE
CERTIFICATE OF CORRECTION

PATENT NO. : 3,954,994
DATED : May 4, 1976
INVENTOR(S) : Gerald F. Holland et al It is certified that error appears in the above-identified patent and that said Letters Patent are hereby corrected as shown below:

Column 3 line 47 change "N" to --H--.

Column 13 line 30 insert --a-- before "mixture".

Column 13 line 31 change "a mixture" to --29--.

Column 18 in the last table change the third line in the chart to
-- O  H  $C_2H_5$  H  134-139  59.99  4.44  60.05  4.50 --.

Column 21 change lines 13 and 14 of the chart to
-- $CF_3O$  $CH_3$  $CH_3$  O  3-Cl --.

Column 34 lines 63-65 change
"4-3'-trifluoromethylsulfonylbenzylthio--
-N-benzyl-N-phenylsulfamylbenzoic  -N-phenylsul-
famylbenzoic acid"

to

-- 4-3'-trifluoromethylsulfonylbenzylthio-3-
N-benzyl-N-phenylsulfamylbenzoic acid --.

Signed and Sealed this

Twenty-sixth Day of April 1977

[SEAL]

Attest:

RUTH C. MASON
Attesting Officer

C. MARSHALL DANN
Commissioner of Patents and Trademarks